US007371375B2

(12) United States Patent
Zimmer et al.

(10) Patent No.: US 7,371,375 B2
(45) Date of Patent: May 13, 2008

(54) PROTEIN

(75) Inventors: Markus Zimmer, Schwerzenbach (CH); Martin Loessner, Binz (CH); Andrew John Morgan, Haywards Heath (GB)

(73) Assignee: PROFOS AG, Regensgurg (DE)

( * ) Notice: Subject to any disclaimer, the term of this patent is extended or adjusted under 35 U.S.C. 154(b) by 0 days.

(21) Appl. No.: 10/503,556

(22) PCT Filed: Jan. 22, 2003

(86) PCT No.: PCT/IB03/00559

§ 371 (c)(1), (2), (4) Date: Mar. 14, 2005

(87) PCT Pub. No.: WO03/066845

PCT Pub. Date: Aug. 14, 2003

(65) Prior Publication Data

US 2005/0153415 A1 Jul. 14, 2005

(30) Foreign Application Priority Data

Feb. 4, 2002 (GB) ................................ 0202556.7

(51) Int. Cl.
*A61K 38/43* (2006.01)
*A61K 38/46* (2006.01)
*A01N 37/18* (2006.01)

(52) U.S. Cl. .......................... 424/94.1; 514/2; 435/7.1; 536/23; 424/94.6

(58) Field of Classification Search ..................... None
See application file for complete search history.

(56) References Cited

U.S. PATENT DOCUMENTS 6,248,324 B1 6/2001 Fischetti et al. ........... 424/94.1
6,254,866 B1 7/2001 Fischetti et al. ........... 424/94.1

FOREIGN PATENT DOCUMENTS

| | | |
|---|---|---|
| EP | 0290295 | 11/1988 |
| EP | 0510907 | 10/1992 |
| WO | WO 00/11472 | 3/2000 |

OTHER PUBLICATIONS

Loessner MJ, Gaeng S, Wendlinger G, Maier SK, Scherer S. The two-component lysis system of *Staphylococcus aureus* bacteriophage Twort: a large TTG-start holin and an associated amidase endolysin. FEMS Microbiol Lett. May 15, 1998;162(2):265-74.*

Songer JG. Clin Microbiol Rev. Clostridial enteric diseases of domestic animals. Apr. 1996;9(2):216-34.*

Loessner MJ, Kramer K, Ebel F, Scherer S. C-terminal domains of *Listeria monocytogenes* bacteriophage murein hydrolases determine specific recognition and high-affinity binding to bacterial cell wall carbohydrates. Mol Microbiol. Apr. 2002;44(2):335-49.*

Young R. Bacteriophage lysis: mechanism and regulation. Microbiol Rev. Sep. 1992;56(3):430-81.*

Bowie, j et al., Deciphering the message in protein sequences: tolerance to amino acid substitutions.Science. 1990 ;247:1306-10.*

STIC Protein Search Report. Tracking No. 171285, pp. 1-3.*

Mims et al., 2004, Medical Microbiology, Third Edition, pp. 9-10, 474-475, 497.*

Scientific Considerations Related to Developing Follo-On Protein Products. Division of Dockets Management U.S. Food and Drug Administration Nov. 12, 2004, pp. 1-12.*

Mims et al., 2004, Medical Microbiology, Third Edition, Mosby, p. 593.*

Gill et al., Bacteriophages and phage-derived products as antibacterial therapeutics.Expert Opinion on Therapeutic Patents Nov. 2007, vol. 17, No. 11, pp. 1341-1350.*

Shimizu et al., "The virR gene, a member of a class of two-component response regulators, regulates the production of perfringolysin O, collagenase, and hemagglutinin in *Clostridium perfringens," J. Bacteriology*, 176:1616-1623, 1994.

Zimmer et al., "Genomic analysis of *Clostridium perfringens* bacteriophage phi3626, which integrates into guaA and possibly affects sporulation," *Journal of Bacteriology*, 184(16):4359-4368, 2002.

Zimmer et al., "The murein hydrolase of the bacteriophage Φ3626 dual lysis system is active against all tested *Clostridium perfringens* strains,"*Applied and Environmental Microbiology*, 68(11):5311-5317, 2002.

Garnier et al., "Complete nucleotide sequence and genetic organization of the bacteriocinogenic plasmid, pIP404, from *Clostridium perfringens," Plasmid*, 19:135-150, 1988.

GenBank Accesssion No. AB016282, Jul. 16, 1998.

Ishikawa et al., "Cloning and expression of two autolysin genes, cwlU and cwlV, which are tandemly arranged on the chromosome of *Bacillus polymyxa* var. colistimus," *Mol. Gen. Genet.*, 262:738-748, 1999.

Kunst et al., "The complete genome sequence of the Gram-positive bacterium *Bacillus subtilis," Nature*, 390:249-256, 1997.

Loessner et al., "Three *Bacillus cereus* bacteriophage endolysins are unrelated but reveal high homology to cell wall hydrolases from different bacilli," *J. Bacteriol.*, 179:2845-28551, 1997.

Lyristis et al., "Identification and molecular analysis of a locus that regulates extracellular toxin production in *Clostridium perfringens.," Mol. Microbiol.*, 12:761-777, 1994.

Nakamura et al., "*Clostridium perfringens*-specific lysin," *Can. J. Microbiol.*, 23:601-606, 1977.

(Continued)

*Primary Examiner*—Joseph Woitach
*Assistant Examiner*—Maria Leavitt
(74) *Attorney, Agent, or Firm*—Fulbright & Jaworski, LLP

(57) ABSTRACT

A nucleic acid comprising a nucleotide sequence encoding a lysin, which nucleotide sequence comprises the sequence shown in SEQ ID No. 1 or a variant, homologue or derivative thereof. A novel lysin obtainable from a bacteriophage capable of colonising *Clostridium perfringens*, and the use thereof as a medicament for the treatment of a disorder associated with pathogenic *Clostridium* bacteria, for example.

14 Claims, 5 Drawing Sheets

OTHER PUBLICATIONS

Cheng et al., "Removal of group B *streptococci* colonizing the vagina and oropharynx of mice with a bacteriophage lytic enzyme," *Antimicrob. Agents Chemother.*, 49:111-117, 2005.

Loeffler et al., "Rapid Killing of *Streptococcus pneumoniae* with Bacteriophage Cell Wall Hydrolase," *Science*, 294:2170-2172, 2001.

Nelson et al., "Prevention and elimination of upper respiratory colonization of mice by group A streptococci by using a bacteriophage lytic enzyme," *Proc. Natl. Acad. Sci. USA*, 98:4107-4112, 2001.

Oldham and Daley, "Lysostaphin: Use of a Recombinant Bactericidal Enzyme as a Mastitis Therapeutic," *J. Dairy Science*, 74:4175-4182, 1991.

Rodriguez-Cerrato et al., "Pneumococcal LytA autolysin, a potent therapeutic agent in experimental peritonitis-sepsis caused by highly beta-lactam-resistant *Streptococcus pneumoniae,*" *Antimicrob. Agents Chemother.*, 51:3371-3373, 2007.

Schuch et al., "A bacteriolytic agent that detects and kills *Bacillus anthracis,*" *Nature*, 418:884-889, 2002.

* cited by examiner

FIGURE 1

SEQ ID No. 1

```
   1 ATGAAGATAG CAGAAAGAGG CGGTCATAAT TTTCAAGCTA CAGGAGCAGT
  51 AGGATTAATA AATGAAACAG TAGAGGATAG AAAAGTATTA GCAGCTGCAT
 101 ACAAATATAC TAAAGCGGCA GGATACGATG TATTAGATGT AACACCAGGC
 151 AATTGTGATT CTAATACAGA TTTAATTTTA GGAGTTAACA AGGCTGAAAG
 201 ATTTGGAGCT GAATTATTCT TAAGTTATCA TTTTGATAAA TGCTATGATG
 251 AATACAATGG AGCTTTAGGA GTTGCTTGTT GGATTTGTGC TACTGGTGGG
 301 AAAGCAGAAG AATACGCTAA AAGCATAGTT GATACTATAG CAGCAGGAAC
 351 AGGATTAAAA AATAGAGGGG TTAAAGTAAA TCCTAAGCTT TATGAATTAA
 401 GGAAAACATC TATGCCAGCA GTTATAGTTG AGGTATGCTT CTGTGAAGCG
 451 ACTGAGGATG TTAGAATTTA CAAAGAAAAA GGTGCAGATT TAATAGGTAA
 501 ATTAATAGCA GAAGGAGTTT GTAAAGTTGC TGGGGGACAA GTTCCAGGAA
 551 CAGTAATAGA AAATGTAGAA TATGAAGTGC AAGAATCTAA ACCAGTTCCA
 601 GTTTATGATA GAAATAAATT TAAAACTAAT GCAAGAGCTT TAGTTAATTT
 651 AGATCCAAGA GATAGAGCAA GTGGAATATA TGAAGATTTA GGCGAAATTT
 701 ATAAGGATGA AAGATTTTAT GTACTTCCAG AGGTTTGTGA TAAAGGTGAT
 751 TATCTGCCAG TTCTTTATTG GAAAGATGGA GCAAATAGAG CATCTAATAA
 801 AGTATGGGTA AGTAGTAAAC AAAAATATAT GATGATAGAC ACTTATCATA
 851 GAGTAGTTAA TGTTGTTACA GAGTTAGATG CTAGATATGA GCCTTCTCCT
 901 AACTCAAATA GAATGGGCTA CGTATGCAAT GCTGAAAGAG TATATGTTCA
 951 TAAGATAGAA GGAAACTATG CATTATGTAC ATATTTTGCA GGAGAAGGCT
1001 ATAAAACAGC ATGGTTTACA GCTAAATATT TAGAAAGAAT ATAA
```

FIGURE 2

SEQ ID No. 2

```
  1  MKIAERGGHN FQATGAVGLI NETVEDRKVL AAAYKYTKAA GYDVLDVTPG
 51  NCDSNTDLIL GVNKAERFGA ELFLSYHFDK CYDEYNGALG VACWICATGG
101  KAEEYAKSIV DTIAAGTGLK NRGVKVNPKL YELRKTSMPA VIVEVCFCEA
151  TEDVRIYKEK GADLIGKLIA EGVCKVAGGQ VPGTVIENVE YEVQESKPVP
201  VYDRNKFKTN ARALVNLDPR DRASGIYEDL GEIYKDERFY VLPEVCDKGD
251  YLPVLYWKDG ANRASNKVWV SSKQKYMMID TYHRVVNVVT ELDARYEPSP
301  NSNRMGYVCN AERVYVHKIE GNYALCTYFA GEGYKTAWFT AKYLERI
```

| | Cl. perfringens strains | other clostridial strains | non-clostridal bacteria |
|---|---|---|---|
| ■ sensitive | 48 | 1 | 0 |
| ▧ non-sensitive | 0 | 25 | 35 |

PROTEIN

This application claims priority to PCT/IB03/00559, filed on Jan. 22, 2003, the entire contents of which are hereby incorporated by reference.

FIELD OF THE INVENTION

The present invention relates to a novel bacterial virus (bacteriophage) lysin and a pharmaceutical composition comprising same.

The present invention further relates to a method of treating a disorder associated with pathogenic *Clostridium* bacteria, in particular *Clostridium perfringens*.

The present invention yet further relates to a method of destroying pathogenic *Clostridium* bacteria, in particular *Clostridium perfringens*.

The present invention also relates to a host transformed with a nucleic acid comprising a nucleotide sequence encoding a bacteriophage lysin.

The present invention further relates to a method of detecting *Clostridium* bacterium, in particular *Clostridium perfringens*, in a sample.

BACKGROUND TO THE INVENTION

*Clostridium perfringens* is a pathogenic bacterium responsible for a variety of disorders, including necrotic enteritis, gas gangrene and food poisoning. *C. perfringens* is predominantly a soil organism. *C. perfringens* is an important pathogenic anaerobe.

There are several habitats in the body (for example, in the intestinal tract and the oral cavity) that are generally anaerobic, and in which obligately anaerobic bacteria can be found as part of the normal flora. However, other parts of the body can become anaerobic as a result of tissue injury or trauma, which results in reduction of blood supply to the injured site, and such anaerobic sites can then become available for colonisation by obligate anaerobes, such as *C. perfringens*.

The presence of *C. perfringens* in the intestinal tract of an animal can result in necrotic enteritis, food poisoning and growth retardation, for example. In particular, the presence of *C. perfringens* in the intestinal tract of poultry, in particular broiler chickens, has been linked with various conditions, such as gut lesions and necrotic enteritis, and can result in a significant reduction in the growth of poultry.

In addition, *C. perfringens* is a causative agent of gas gangrene, which can occur as a result of tissue injury or trauma and thus an anaerobic environment, which is suitable for colonisation by obligate anaerobes, such as *C. perfringens*.

Like viruses in general, bacteriophages can be divided into those with RNA genomes (mostly small and single stranded), those with small DNA genomes (generally less than 10 kb, mostly single stranded) and those with medium to large DNA genomes (30-200 kb).

The genes in bacteriophages are clustered into early stage and late stage genes.

In virulent phages, the genes whose products are needed for phage DNA synthesis and host DNA breakdown, including those mediating nucleotide metabolism and the proteins that make up the replication complex, are all expressed immediately after infection. With time, early synthesis is shut off and other genes that code for virion components and lysis genes are activated. The shutoff of early genes is effected both at the transcriptional and the translational level.

In temperate phages, the phage may undergo lysogeny, wherein genes are switched on upon infection which cause integration of the phage into the host genome such that the phage is propagated indirectly by this means. The lysogenic state, once established, is quite stable. Environmental events that harm the lysogenic bacterial host can cause the lysogenic state to break down and can trigger the lytic life cycle of the integrated phage. At which point, the phage switches to gene (both early and late) which cause the lytic life cycle.

Once the late genes are expressed in both virulent and temperate phages, the stage is set for assembling virions. The heads, tails, tail fibres and soluble protein catalysing tail fibre addition are all made separately. The heads and tails typically combine first to form complexes and finally tail fibres are added to the complex.

The final stage of the cycle is cellular lysis, releasing virions into the medium. Lysis usually requires two gene products: a lysin, which attacks the bonds joining N-acetylglucosamines in the rigid murein layer; and a holin, which creates holes in the inner membrane, allowing the lysin to reach its substrate.

Thus, bacteriophage lysins are phage-encoded cell wall hydrolysing enzymes which are synthesised during late gene expression in the lytic cycle of phage multiplication and mediate the release of progeny virions from infected cells through degradation of the bacterial peptidoglycan.

EP 0 510 907 discloses a lysin from phages of *Listeria monocytogenes* and formulations of such a lysin substantially free of the bacteriophage itself, together with a method of destroying *L. monocytogenes*. Although EP 0 510 907 also suggests the use of a lysin from phages of *Clostridium tyrobutyricum*, the specification does not show how to obtain such an isolated lysin nor the sequence thereof.

WO00/11472 teaches a detection method using cell wall binding domains of proteins and/or enzymes.

Prior to the present invention the lytic cycle of bacteriophages that infect *C. perfringens* have been little studied.

The term "bacteriophage" as used herein is to be regarded as being interchangeable with the term "phage".

SUMMARY ASPECTS

A seminal finding of the present invention is the identification and sequencing of a nucleotide sequence encoding a lysin from a bacteriophage capable of colonising pathogenic *Clostridium* bacteria, in particular *Clostridium perfringens*, and the use of such a lysin to lyse pathogenic *Clostridium* bacteria, in particular pathogenic *Clostridium perfringens* bacteria.

DETAILED ASPECTS

In one aspect the present invention relates to a lysin obtainable from a bacteriophage capable of colonising *Clostridium perfringens*. Preferably said lysin is in a substantially pure form.

The present invention further relates to a lysin in substantially pure form comprising the amino acid sequence shown in SEQ ID No. 2 or a variant, homologue or derivative thereof.

In a further aspect the present invention relates to a nucleic acid comprising a nucleotide sequence encoding a lysin comprising the amino acid sequence shown in SEQ ID No. 2 or a variant, homologue or derivative thereof.

In a further aspect the present invention relates to a nucleic acid comprising a nucleotide sequence encoding a lysin, which nucleotide sequence is shown in SEQ ID No. 1 or a variant, homologue or derivative thereof.

In a yet further aspect, the invention relates to a nucleic acid comprising a nucleotide sequence selected from:

(a) the nucleotide sequence presented as SEQ ID No. 1;

(b) a nucleotide sequence that is a variant, homologue, derivative or fragment of the nucleotide sequence presented as SEQ ID No. 1;

(c) a nucleotide sequence that is the complement of the nucleotide sequence set out in SEQ ID No. 1;

(d) a nucleotide sequence that is the complement of a variant, homologue, derivative or fragment of the nucleotide sequence presented as SEQ ID No. 1;

(e) a nucleotide sequence that is capable of hybridising to the nucleotide sequence set out in SEQ ID No. 1;

(f) a nucleotide sequence that is capable of hybridising to a variant, homologue, derivative or fragment of the nucleotide sequence presented as SEQ ID No. 1;

(g) a nucleotide sequence that is the complement of a nucleotide sequence that is capable of hybridising to the nucleotide sequence set out in SEQ ID No. 1;

(h) a nucleotide sequence that is the complement of a nucleotide sequence that is capable of hybridising to a variant, homologue, derivative or fragment of the nucleotide sequence presented as SEQ ID No. 1;

(i) a nucleotide sequence that is capable of hybridising to the complement of the nucleotide sequence set out in SEQ ID No. 1;

(j) a nucleotide sequence that is capable of hybridising to the complement of a variant, homologue, derivative or fragment of the nucleotide sequence presented as SEQ ID No. 1;

(k) a nucleotide sequence comprising any one of (a), (b), (c), (d), (e), (f), (g), (h), (i), and/or (j).

In a further aspect, the present invention relates to a nucleic acid comprising a nucleotide sequence encoding a lysin, which nucleotide sequence is selected from the group consisting of:

(a) a nucleotide sequence comprising the sequence shown in SEQ ID No. 1;

(b) a nucleotide sequence which is complementary to a nucleotides sequence which hybridises under high and/or intermediate stringency conditions with the sequence shown in SEQ ID No. 1; and (c) a nucleotide sequence which is related to the nucleotide sequence of SEQ ID No. 1 by the degeneration of the genetic code.

In a further aspect the present invention relates to a substantially pure lysin obtainable or obtained from the expression of the nucleic acid comprising the nucleotide sequence according to the present invention.

In a further aspect the present invention provides a host transformed with a nucleic acid comprising a nucleotide sequence encoding a lysin according to the present invention.

EP 0 510 907 discloses a microbial host transformed with means to express a lysin of a phage of *Listeria monocytogenes*. The teachings of EP 0 510 907 may be adapted in accordance with the present invention.

A further aspect of the present invention provides a host transformed with a nucleic acid comprising a nucleotide sequence shown in SEQ ID No. 1 or a variant, homologue or derivative thereof.

The present invention yet further provides a lysin derived from the cultivation of a host according to the present invention. Preferably, the lysin is in a substantially pure form.

In a further aspect the present invention relates to a composition, preferably a pharmaceutical composition, comprising a lysin according to the present invention and/or a host transformed with a nucleic acid comprising a nucleotide sequence encoding a lysin according to the present invention.

The present invention also relates to a lysin according to the present invention and/or a host transformed with a nucleic acid comprising a nucleotide sequence encoding a lysin according to the present invention for use as a medicament.

In a further aspect the present invention relates to the use of a lysin according to the present invention and/or a host transformed with a nucleic acid comprising a nucleic acid comprising a nucleic acid comprising a nucleotide sequence encoding a lysin according to the present invention in the manufacture of a medicament for the treatment of a disorder, disease or condition associated with pathogenic *Clostridium* species, preferably with pathogenic *C. perfringens*.

In a further aspect the present invention relates to the use of a lysin according to the present invention and/or a host transformed with a nucleic acid comprising a nucleotide sequence encoding a lysin according to the present invention in the manufacture of a medicament for the treatment of reduced weight gain caused by pathogenic *Clostridium* species, preferably with pathogenic *C. perfringens*, in the intestinal tract of poultry, preferably chickens.

In a further aspect the present invention relates to the use of a lysin in substantially pure form comprising the amino acid sequence shown in SEQ ID No. 2 or an amino acid sequence having at least 80% homology therewith in the manufacture of a medicament for the treatment of reduced weight gain caused by pathogenic *Clostridium* species, preferably with pathogenic *C. perfringens*, in the intestinal tract of poultry, preferably chickens.

The present invention further relates to a medicament comprising a lysin according to the present invention and/or a host transformed with a nucleic acid comprising a nucleotide sequence encoding a lysin according to the present invention.

The present invention further relates to a medicament comprising a lysin in substantially pure form comprising the amino acid sequence shown in SEQ ID No. 2 or an amino acid sequence having at least 80% homology therewith and/or a host transformed with a nucleic acid comprising a nucleotide sequence encoding a lysin comprising the amino acid sequence shown in SEQ ID No. 2 or an amino acid sequence having at least 80% homology therewith.

In a further aspect the present invention relates to a method of treating a disorder, disease or condition in a subject in need of treatment, which method comprises administering to said subject an effective amount of a lysin according to the present invention and/or an effective amount of a host transformed with a nucleic acid comprising a nucleotide sequence encoding a lysin according to the present invention or a composition according to the present invention.

In a further aspect the present invention relates to a method of treating reduced weight gain in poultry, preferably chickens, which method comprises administering to said poultry an effective amount of a lysin according to the present invention and/or an effective amount of a host transformed with a nucleic acid comprising a nucleotide sequence encoding a lysin according to the present invention or a composition according to the present invention.

In a further aspect the present invention relates to a method of treating reduced weight gain in poultry, preferably chickens, which method comprises administering to said poultry an effective amount of a lysin in substantially pure form comprising the amino acid sequence shown in SEQ ID No. 2 or an amino acid sequence having at least 80% homology therewith and/or a host transformed with a nucleic acid comprising a nucleotide sequence encoding a lysin comprising the amino acid sequence shown in SEQ ID No. 2 or an amino acid sequence having at least 80% homology therewith.

The present invention also relates to a pharmaceutical pack comprising one or more compartments, wherein at least one compartment comprises one or more lysins according to the present invention and/or one or more hosts transformed with a nucleic acid comprising a nucleotide sequence encoding a lysin according to the present invention or a composition according to the present invention.

The present invention also relates to a pharmaceutical pack comprising one or more compartments, wherein at least one compartment comprises one or more lysins in substantially pure form comprising the amino acid sequence shown in SEQ ID No. 2 or an amino acid sequence having at least 80% homology therewith and/or one or more hosts transformed with a nucleic acid comprising a nucleotide sequence encoding a lysin comprising the amino acid sequence shown in SEQ ID No. 2 or an amino acid sequence having at least 80% homology therewith.

In another aspect the present invention relates to a process of preparation of a pharmaceutical composition, said process comprising admixing one or more lysins according to the present invention and/or one or more hosts transformed with a nuclei acid comprising a nucleotide sequence encoding a lysin according to the present invention with a pharmaceutically acceptable diluent, excipient or carrier.

In another aspect the present invention relates to a process of preparation of a pharmaceutical composition, said process comprising admixing one or more lysins in substantially pure form comprising the amino acid sequence shown in SEQ ID No. 2 or an amino acid sequence having at least 80% homology therewith and/or one or more hosts transformed with a nucleic acid comprising a nucleotide sequence encoding a lysin comprising the amino acid sequence shown in SEQ ID No. 2 or an amino acid sequence having at least 80% homology therewith with a pharmaceutically acceptable diluent, excipient or carrier.

The present invention further relates to a method of destroying a pathogenic bacterium of the genera *Clostridium*, which method comprises lysing a pathogenic *Clostridium* bacterium with a substantially pure lysin according to the present invention or a composition according to the present invention.

The present invention further relates to a method of destroying a pathogenic bacterium of the genera *Clostridium*, which method comprises lysing a pathogenic *Clostridium* bacterium with a lysin in substantially pure form comprising the amino acid sequence shown in SEQ ID No. 2 or an amino acid sequence having at least 80% homology therewith or a composition comprising said lysin.

In a yet further aspect the present invention provides an expression vehicle comprising a nucleic acid comprising a nucleotide sequence according to the present invention and regulatory regions associated therewith for expression of the coding sequence in a suitable host.

The present invention further provides the use of a lysin according to present invention and/or a host transformed with a nucleic acid comprising a nucleotide sequence encoding a lysin according to the present invention in the manufacture of a medicament for the treatment of a growth disorder in poultry, which growth disorder is caused by the colonisation of the poultry's intestinal tract, or part thereof, by *Clostridium perfringens*.

The present invention further provides a method of detecting a pathogenic *Clostridium* bacterium, preferably *Clostridium perfringens*, in a sample, using a diagnostic marker based on a lysin according to the present invention or a mimetic thereof.

The present invention also provides a method of detecting a pathogenic *Clostridium* bacterium, preferably *Clostridium perfringens*, in a sample, using a diagnostic marker based on a lysin comprising the amino acid sequence shown in SEQ ID No. 2 or an amino acid sequence having at least 80% homology therewith or a mimetic thereof.

The term "based on" as used herein means that the diagnostic marker comprises a lysin according to the present invention or a portion thereof. Suitably, at least both the lytic portion and the cell-wall binding domain portion of the lysin according to the present invention may be used. In which case, the lytic portion thereof may be fully functional, i.e. capable of lysing bacterial cells, or may be modified in such a way as to change and/or switch off the lysing function of the lysin. A suitable method of modifying said lysin may be by use of random and/or site directed mutagenesis. The diagnostic marker may suitably comprise only the cell wall binding domain portion or part thereof of the lysin.

The diagnostic marker may comprise a marker which is readily identifiable. Suitable markers includes reporters, including reporters detailed in the section herein entitled "Reporter". The marker may be bonded directly or indirectly to the lysin or a portion thereof. By way of example only, a suitable reporter may include a fluorescent protein. The reporter may be coupled either directly or indirectly to the lysin or a portion thereof.

When it is the case that the bacterial cells are lysed by the diagnostic marker, the lysis of one or more bacterial cells may be monitored. The lysis may be monitored optically for example. The lysis may be monitored by measuring the cellular contents released by the lysis of the bacterial cells, for example the release of ATP may be measured by bioluminescence.

The diagnostic marker may comprise a solid phase (for example, but not exclusively, activated polystyrene, activated glass, silicon or glass-like materials, activated latex, gold or gold compounds, various ferromagnetic carrier materials, hydrophobic or electrically charged synthetic materials) attached either directly or indirectly to the lysin or a portion thereof. Such that cells capable of bonding to said lysin or portion thereof can be immobilised onto or against said solid phase.

The advantages of the detection method according to the present invention is that it is not species specific, it is easier than raising antibodies to the *Clostridium* bacterium, and/or both binding and detection can be achieved easily.

In a further aspect, the present invention provides the cell wall binding domain portion or part thereof of a lysin according to the present invention for use in drug delivery.

In a yet further aspect, the present invention provides a method for screening databases for alternative polypeptides for use in accordance with the present invention, wherein said method comprises screening a database using the amino acid sequence shown in SEQ ID No. 2, and selecting one or more amino acid sequences which is/are homologous with the amino acid sequence shown in SEQ ID No. 2. Preferably, the sequences are at least 80% homologous with the amino acid sequence shown in SEQ ID No. 2.

In a further aspect, the present invention provides a method for modifying a lysin according to the present invention in order to alter the lytic activity of the lysin in respect of one or more bacterial species.

The lysin according to the present invention may be modified in order to enhance the bacterial spectrum upon which the lysin is active. Alternatively, the lysin may be modified in order to focus the activity thereof to a specific bacterial species and/or strain; in other words, to increase the host specificity thereof.

For ease of reference, these and further aspects of the present invention are now discussed under appropriate section headings. However, the teachings under each section are not necessarily limited to each particular section.

PREFERABLE ASPECTS

Preferably, the nucleic acid according to the present invention is in a substantially pure form.

Preferably, the nucleic acid according to the present invention is in an isolated form.

Preferably, the nucleic acid comprising the nucleotide sequence according to the present invention is obtainable from a bacteriophage capable of infecting and/or colonising *Clostridium perfringens.*

Suitably, the nucleic acid and/or lysin according to the present invention obtained from a bacteriophage capable of infecting and/or colonising *Clostridium perfringens.*

Preferably, the nucleic acid according to the present invention is obtainable or obtained from a bacteriophage, which has infected and/or colonised *Clostridium perfringens.*

Preferably, the nucleic acid and/or lysin according to the present invention is obtainable or obtained from bacteriophage φ3626 or from bacteriophage φ8533.

Preferably, the pharmaceutical composition according to the present invention further comprises a pharmaceutically acceptable diluent, excipient or carrier.

Preferably, the disorder, disease and/or condition is one associated with pathogenic *Clostridium* species, preferably *Clostridium perfringens.*

Suitable disorders, diseases and/or conditions include necrotic enteritis, gas gangrene, food poisoning, gut lesions and reduced weight gain, for example.

As stated above, *Clostridium* species, particularly *C. perfringens*, in the intestinal tract of certain animals, in particular poultry, such as broiler chickens, has been associated with reduced growth potential in these animals compared with uninfected animals. The effect is most pronounced if the number of bacteria in the intestinal tract exceeds a threshold level. For example, the threshold level will typically be about $10^6$-$10^8$ cfu/g. The lysin according to the present invention and/or a host comprising a lysin according to the present invention may be used in the treatment of this reduced growth potential. In other words, the lysin according to the present invention and/or a host comprising a lysin according to the present invention may be used to control the number of bacteria in the intestinal tract of the animals, in particular poultry, such as broiler chickens, thus to enhance weight gain in said animals. In one embodiment, the lysin according to the present invention and/or a host comprising a lysin according to the present invention may completely eliminate said bacteria in the intestinal tract of said animal. In an alternative embodiment, the lysin and/or host may reduce the number of said bacteria to below a threshold level, i.e. that level which results in a reduction in weight gain in the animal.

Preferably, the host according to the present invention is a microbial host.

Preferably, the host according to the present invention is a food-grade microorganism.

Preferably, the host according to the present invention is a gut-colonising organism.

Suitably, the host may be an organism, preferably microorganism, which is generally-recognised-as-safe (GRAS).

Preferably, the microbial host according to the present invention is one or more microorganisms from the following genera: *Escherichia, Lactobacillus, Bacillus, Lactococcus, Staphylococcus, Pediococcus.*

In a preferred aspect the microbial host is a bacterium from one or more of the following species: *Escherichia coli, Lactobacillus acidophilus, Staphylococcus carnosus* or related species.

Preferably, the nucleic acid in said host comprises one or more signal sequences which direct secretion of the lysin of the present invention coding sequences through the host's cell membrane.

Preferably, the lysin according to the present invention is in a substantially pure form.

Preferably, the lysin according to the present invention is in an isolated form.

Preferably, the *Clostridium* bacterium as mentioned herein is of the *Clostridium perfringens* species.

Preferably, the *Clostridium* bacterium as mentioned herein is in the intestinal tract of a subject.

Suitably, the *Clostridium* bacterium may be in a food or a beverage.

Suitably, the lysin according to the present invention may be modified, such as by random or site-specific mutagenesis.

DETAILED DESCRIPTION OF THE INVENTION

Although in general any molecular techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed., John Wiley & Sons, Inc.

Lysin

The term “lysin” as used herein incorporates the term “endolysin”. The term “lysin” as used herein means any agent, such as an enzyme or a toxin, which is capable of lysing cells.

Agent

The term “agent” as used herein means a lysin according to the present invention and/or a host transformed with a nucleic acid comprising a nucleotide sequence encoding a lysin according to the present invention.

Medicament

The term “medicament” as used herein encompasses medicaments for both human and animal usage in human and veterinary medicine. In addition, the term “medicament” as used herein encompasses a product designed for incorporation in animal feed, particularly poultry feed.

Treatment

It is to be appreciated that all references herein to treatment include curative, palliative and prophylactic treatment.

Recombinant Methods

Typically the nucleotide sequence of the present invention may be prepared by recombinant DNA techniques.

Amino Acid Sequence

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

The amino acid sequence may be prepared by isolation from a suitable source or it may be made synthetically or it may be prepared by use of recombinant DNA techniques.

In one aspect, the present invention provides an amino acid sequence that is a lysin capable of hydrolysing the cell walls of pathogenic *Clostridium* bacteria, preferably *Clostridium perfringens* bacteria.

Preferably, the lysin comprises the amino acid sequence shown in SEQ ID No. 2 or a variant, derivative or homologue thereof.

Preferably, the lysin is an isolated lysin and/or is a substantially isolated lysin and/or is purified and/or is substantially purified and/or is non-native. Thus the lysin may be in a pure or substantially pure form.

It will be understood that the lysin according to the present invention may be mixed with carriers or diluents which will not interfere with the intended purpose of the lysin and which will still be regarded as pure and/or isolated.

Nucleotide Sequence

As used herein, the term "nucleotide sequence" is synonymous with the term "polynucleotide".

The nucleotide sequence may be DNA or RNA of genomic or synthetic or of recombinant origin. The nucleotide sequence may be double-stranded or single-stranded whether representing the sense or antisense strand or combinations thereof.

For some applications, preferably, the nucleotide sequence is DNA.

For some applications, preferably, the nucleotide sequence is prepared by use of recombinant DNA techniques (e.g. recombinant DNA).

For some applications, preferably, the nucleotide sequence is cDNA.

For some applications, preferably, the nucleotide sequence may be the same as the naturally occurring form for this aspect.

In one aspect of the present invention the nucleotide sequence encodes a lysin capable of hydrolysing the cell wall of *Clostridium* bacteria, preferably *Clostridium perfringens* bacteria.

It will be understood by a skilled person that numerous different nucleotide sequences can encode the same lysin as a result of the degeneracy of the genetic code. In addition, it is to be understood that skilled persons may, using routine techniques, make nucleotide substitutions that do not substantially affect the activity encoded by the nucleotide sequence of the present invention to reflect the codon usage of any particular host organism in which the target is to be expressed. Thus, the terms "variant", "homologue" or "derivative" in relation to the nucleotide sequence set out in the attached sequence listings include any substitution of, variation of, modification of, replacement of, deletion of or addition of one (or more) nucleotide from or to the sequence providing the resultant nucleotide sequence encodes a functional lysin according the present invention.

As indicated above, with respect to sequence homology, preferably there is at least 75%, more preferably at least 85%, more preferably at least 90% homology to SEQ ID No. 1 shown herein. More preferably there is at least 95%, more preferably at least 98%, homology. Nucleotide homology comparisons may be conducted as described below. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length. These sequences could be used a probes, such as in a diagnostic kit.

Variants/Homologues/Derivatives

In addition to the specific nucleotide and amino acid sequences mentioned herein and amino acid sequences derivable from said nucleotide sequences, the present invention also encompasses the use of variants, homologue and derivatives thereof. Here, the term "homology" can be equated with "identity".

In the present context, a homologous sequence is taken to include an amino acid sequence or a nucleotide sequence which may be at least 75, 85 or 90% identical, preferably at least 95 or 98% identical. In particular, homology should typically be considered with respect to those regions of the sequence known to be essential for an activity. Although homology can also be considered in terms of similarity (i.e. amino acid residues having similar chemical properties/functions), in the context of the present invention it is preferred to express homology in terms of sequence identity.

In a preferred aspect, the variant, homologue or derivative is a nucleotide sequence which is at least 75, 85 or 90% identical, preferably at least 95 or 98% identical, with SEQ ID No. 1.

In a further aspect, the variant, homologue or derivative is a nucleotide sequence which is at least 75, 85 or 90% identical, preferably at least 95 or 98% identical, with that part of the sequence shown in SEQ ID No. 1 which encodes the cell wall binding domain.

In a preferred aspect, the variant, homologue or derivative is an amino acid which is at least 75, 85 or 90% identical, preferably at least 95 or 98% identical, with the amino acid sequence shown in SEQ ID No. 2.

In a further aspect, the variant, homologue or derivative is an amino acid which is at least 75, 85 or 90% identical, preferably at least 95 or 98% identical, with the cell wall binding domain of the sequence shown in SEQ ID No. 2.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Hybridisation

The term "hybridisation" as used herein shall include "the process by which a strand of nucleotide sequence joins with a complementary strand through base pairing" as well as the process of amplification as carried out in polymerase chain reaction (PCR) technologies.

Nucleotide sequences of the invention capable of selectively hybridising to the nucleotide sequences presented herein, or to their complement, will be generally at least 75%, preferably at least 85 or 90% and more preferably at least 95% or 98% homologous to the corresponding complementary nucleotide sequences presented herein over a region of at least 20, preferably at least 25 or 30, for instance at least 40, 60 or 100 or more contiguous nucleotides.

The term "selectively hybridisable" means that the nucleotide sequence, when used as a probe, is used under conditions where a target nucleotide sequence is found to hybridise to the probe at a level significantly above background. The background hybridisation may occur because of other nucleotide sequences present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

In a preferred aspect the variant, homologue or derivative according to the present invention hybridises to the nucleotide sequence shown in SEQ ID No 1 under high stringency and/or intermediate stringency conditions.

In another aspect the variant, homologue or derivative according to the present invention is capable of selectively hybridising to the nucleotide sequences shown as SEQ ID No. 1, or to their complement, under high stringency and/or intermediate stringency, and will be generally at least 75%, preferably at least 85 or 90% and more preferably at least 95% or 98% homologous to the corresponding complementary nucleotide sequence shown in SEQ ID No. 1 over a region of at least 20, preferably at least 25 or 30, for instance at least 40, 60 or 100 or more contiguous nucleotides.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M $Na_3$ Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

Nucleotide sequences which are not 100% homologous to the sequences of the present invention but fall within the scope of the invention can be obtained in a number of ways. Other variants of the sequences described herein may be obtained for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the nucleotide sequence set out in herein under conditions of medium to high stringency. Similar considerations apply to obtaining species homologues and allelic variants of the amino acid and/or nucleotide sequences of the present invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used. The primers used in degenerate PCR will contain one or more degenerate positions and will be used at stringency conditions lower than those used for cloning sequences with single sequence primers against known sequences.

Alternatively, such nucleotide sequences may be obtained by site directed mutagenesis of characterised sequences, such as the nucleotide sequence set out in SEQ ID No 1 of the sequence listings of the present invention. This may be useful where for example silent codon changes are required to sequences to optimise codon preferences for a particular host cell in which the nucleotide sequences are being expressed. Other sequence changes may be desired in order to introduce restriction enzyme recognition sites, or to alter the activity of the protein encoded by the nucleotide sequences.

The nucleotide sequences of the present invention may be used to produce a primer, e.g. a PCR primer, a primer for an alternative amplification reaction, a probe e.g. labelled with a revealing label by conventional means using radioactive or non-radioactive labels, or the nucleotide sequences may be cloned into vectors. Such primers, probes and other fragments will be at least 15, preferably at least 20, for example at least 25, 30 or 40 nucleotides in length, and are also encompassed by the term nucleotide sequence of the invention as used herein.

The nucleotide sequences such as a DNA polynucleotides and probes according to the invention may be produced recombinantly, synthetically, or by any means available to those of skill in the art. They may also be cloned by standard techniques.

In general, primers will be produced by synthetic means, involving a step-wise manufacture of the desired nucleotide sequence one nucleotide at a time. Techniques for accomplishing this using automated techniques are readily available in the art.

Longer nucleotide sequences will generally be produced using recombinant means, for example using a PCR (polymerase chain reaction) cloning techniques. This will involve making a pair of primers (e.g. of about 15 to 30 nucleotides) flanking a region of the targeting sequence which it is desired to clone, bringing the primers into contact with mRNA or cDNA obtained from an animal or human cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Due to the inherent degeneracy of the genetic code, other DNA sequences which encode substantially the same or a functionally equivalent amino acid sequence, may be used to clone and express the target sequences. As will be understood by those of skill in the art, for certain expression systems, it may be advantageous to produce the target sequences with non-naturally occurring codons. Codons preferred by a particular prokaryotic or eukaryotic host (Murray E et al (1989) Nuc Acids Res 17:477-508) can be selected, for example, to increase the rate of the target expression or to produce recombinant RNA transcripts having desirable properties, such as a longer half-life, than transcripts produced from naturally occurring sequence.

Substantially Pure Form and/or Isolated Form

Preferably, the lysin according to the present invention or nucleotide comprising the nucleotide sequence coding for same is in a substantially pure form or is in an isolated form.

The term "substantially pure form" is used to indicate that the component, for example a lysin according to the present invention and/or a nucleotide comprising a nucleotide sequence according to the present invention, is present at a high level. The component, i.e. a lysin according to the present invention and/or nucleotide comprising a nucleotide sequence encoding a lysin according to the present invention, is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration.

At very high levels (e.g. at levels of more than 90%, of more than 95% or of more than 99%) the component may be regarded as being "isolated". Biologically active substances of the present invention (including polypeptides, nucleic acid molecules, moieties identified/identifiable via screening, etc.) may be provided in a form that is substantially free of one or more contaminants with which the substance might otherwise be associated. Thus, for example, they may be substantially free of one or more potentially contaminating polypeptides and/or nucleic acid molecules. They may be provided in a form that is substantially free of other cell components (e.g. of cell membranes, of cytoplasm, etc.). When a composition is substantially free of a given contaminant, the contaminant will be at a low level (e.g. at a level of less than 10%, less than 5% or less than 1% on the dry weight/dry weight basis set out above).

Pharmaceutically Acceptable Salt

The lysin according to the present invention may be in the form of—and/or may be administered as—a pharmaceutically acceptable salt—such as an acid addition salt or a base salt—or a solvate thereof, including a hydrate thereof. For a review on suitable salts see Berge et al, J. Pharm. Sci., 1977, 66, 1-19.

Typically, a pharmaceutically acceptable salt may be readily prepared by using a desired acid or base, as appropriate. The salt may precipitate from solution and be collected by filtration or may be recovered by evaporation of the solvent.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc, diolamine, olamine, ethylenediamine, tromethamine, chloine, megulamine and diethanolamine salts. For reviews on suitable pharmaceutical salts see Berge et al J. Pharm. Sci., 66, 1-19 (1977); Gould P. L., International J. of Pharmaceutics, 33 (1986), 201-217; and Bighley et al, Encyclopaedia of Pharmaceutical Technology, Marcel Dekker Inc., New York (1996), Vol. 13, page 453-497.

The pharmaceutically acceptable solvates of the compound of the invention, i.e. of the lysin, include the hydrates thereof.

Hereinafter, compounds, including the lysin according to their present invention or a host transformed with a nucleic acid comprising the nucleotide sequence encoding the lysin according to the present invention, their pharmaceutically acceptable salts, their solvates and polymorphs, defined in any aspect of the invention (except intermediate compounds in chemical processes) are referred to as "compounds of the invention" or "agents of the invention".

Polymorphic Form(s)/Asymmetric Carbon(s)

The agent, e.g. lysin, may exist in polymorphic form.

The agent may contain one or more asymmetric carbon atoms and therefore exists in two or more stereoisomeric forms. Where an agent contains an alkenyl or alkenylene group, cis (E) and trans (Z) isomerism may also occur. The present invention includes the individual stereoisomers of the agent and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Isotopic Variations

The present invention also includes all suitable isotopic variations of the lysin or a pharmaceutically acceptable salt thereof. An isotopic variation of a lysin of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the lysin and pharmaceutically acceptable salts thereof can generally be prepared by conventional procedures using appropriate isotopic variations of suitable reagents.

Prodrugs

It will be appreciated by those skilled in the art that the lysin of the present invention may be derived from a prodrug. Examples of prodrugs include entities that have certain protected group(s) and which may not possess pharmacological activity as such, but may, in certain instances, be administered (such as orally or parenterally) and thereafter metabolised in the body to form the agent which are pharmacologically active.

All protected derivatives and prodrugs of compounds of the present invention are included within the scope of the invention.

Pro-Moieties

It will be further appreciated that certain moieties known as "pro-moieties", for example as described in "Design of Prodrugs" by H. Bundgaard, Elsevier, 1985 (the disclosure of which is hereby incorporated by reference), may be placed on appropriate functionalities of the agents. Such prodrugs are also included within the scope of the invention.

Pharmaceutical Compositions

The present invention also provides a pharmaceutical composition comprising a therapeutically effective amount of the agent of the present invention, i.e. a lysin according to the present invention, and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. In one preferred embodiment the pharmaceutical composition may be for use in poultry, in particular broiler chickens.

Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

In a preferred embodiment, the agents of the present invention are delivered systemically (such as orally, buccally, sublingually), more preferably orally.

Hence, preferably the agent is in a form that is suitable for oral delivery.

Administration

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The agent of the present invention, i.e. a lysin of the present invention and/or a host transformed with a nucleic acid comprising a nucleotide sequence encoding a lysin according to the present invention, may be administered alone but will generally be administered as a pharmaceutical composition—e.g. when the agent is in admixture with a suitable pharmaceutical excipient, diluent or carrier selected with regard to the intended route of administration and standard pharmaceutical practice.

For example, the agent can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The agent, i.e. a lysin of the present invention and/or a host transformed with a nucleic acid comprising a nucleotide sequence encoding a lysin according to the present invention may be administered in animal feed or fodder, or as an animal feed or fodder supplement. In particular, the lysin of the present invention and/or a host transformed with a nucleic acid comprising nucleotide sequence encoding a lysin according to the present invention may be incorporated into or added to the feed of poultry.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, penile, vaginal, epidural, sublingual.

It is to be understood that a lysin according to the present invention and/or a host transformed with a nucleic acid comprising a nucleotide sequence encoding a lysin according to the present invention need not be administered by the same route. Likewise, if the composition comprises more than one active component, then those components may be administered by different routes.

If the agent of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the agent of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the agent of the present invention can be administered in the form of a suppository or pessary, or it may be applied topically in the form of a gel, hydrogel, lotion, solution, cream, ointment or dusting powder. The agent of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compositions of the present invention may be administered by direct injection.

For some applications, preferably the agent is administered orally.

Dose Levels

Typically, a physician or veterinary surgeon will determine the actual dosage which will be most suitable for an individual subject. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

The agent and/or the pharmaceutical composition of the present invention may be administered in accordance with a regimen of from 1 to 10 times per day, such as once or twice per day.

For oral and parenteral administration to humans or animals, the daily dosage level of the agent may be in single or divided doses.

Depending upon the need, the agent may be administered at a dose of from 0.01 to 30 mg/kg body weight, such as from 0.1 to 10 mg/kg, more preferably from 0.1 to 1 mg/kg body weight. Naturally, the dosages mentioned herein are exemplary of the average case. There can, of course, be individual instances where higher or lower dosage ranges are merited.

Typically the daily oral dose may be, for instance, between 20-1000 mg, preferably 50-300 mg for example.

Suitable doses will include those which allow a therapeutic reduction in the number of pathogenic bacteria of the genera *Clostridium*, in particular of *C. perfringens* bacteria.

Formulation

The agents of the present invention may be formulated into a pharmaceutical composition, such as by mixing with one or more of a suitable carrier, diluent or excipient, by using techniques that are known in the art.

Subject

As used herein, the term "subject" refers to vertebrates, particularly members of the mammalian species. The term includes but is not limited to, domestic animals, sports animals, agricultural livestock, primates and humans. The term "agricultural livestock" encompasses poultry, for example broiler chickens.

Bioavailability

Preferably, the compounds of the invention (and combinations) are orally bioavailable. Oral bioavailability refers to the proportion of an orally administered drug that reaches the systemic circulation. The factors that determine oral bioavailability of a drug are dissolution, membrane permeability and metabolic stability. Typically, a screening cascade of firstly in vitro and then in vivo techniques is used to determine oral bioavailability.

Dissolution, the solubilisation of the drug by the aqueous contents of the gastro-intestinal tract (GIT), can be predicted from in vitro solubility experiments conducted at appropriate pH to mimic the GIT. Preferably the compounds of the invention have a minimum solubility of 50 mcg/ml. Solubility can be determined by standard procedures known in the art such as described in Adv. Drug Deliv. Rev. 23, 3-25, 1997.

Membrane permeability refers to the passage of the compound through the cells of the GIT. Lipophilicity is a key property in predicting this and is defined by in vitro Log $D_{7.4}$ measurements using organic solvents and buffer. Preferably the compounds of the invention have a Log $D_{7.4}$ of −2 to +4, more preferably −1 to +2. The log D can be determined by standard procedures known in the art such as described in J. Pharm. Pharmacol. 1990, 42:144.

Cell monolayer assays such as $CaCO_2$ add substantially to prediction of favourable membrane permeability in the presence of efflux transporters such as p-glycoprotein, so-called caco-2 flux. Preferably, compounds of the invention have a caco-2 flux of greater than $2\times10^{-6}$ $cms^{-1}$, more preferably greater than $5\times10^{-6}$ $cms^{-1}$. The caco flux value can be determined by standard procedures known in the art such as described in J. Pharm. Sci, 1990, 79, 595-600.

Metabolic stability addresses the ability of the GIT or the liver to metabolise compounds during the absorption process: the first pass effect. Assay systems such as microsomes, hepatocytes etc are predictive of metabolic liability. Preferably the agents of the present invention show metabolic stability in the assay system that is commensurate with an hepatic extraction of less then 0.5. Examples of assay systems and data manipulation are described in Curr. Opin. Drug Disc. Devel., 201, 4, 36-44, Drug Met. Disp., 2000, 28, 1518-1523.

Because of the interplay of the above processes further support that a drug will be orally bioavailable in humans can be gained by in vivo experiments in animals. Absolute bioavailability is determined in these studies by administering the agent separately or in mixtures by the oral route. For absolute determinations (% absorbed) the intravenous route is also employed. Examples of the assessment of oral bioavailability in animals can be found in Drug Met. Disp., 2001, 29, 82-87; J. Med Chem, 1997, 40, 827-829, Drug Met. Disp., 1999, 27, 221-226.

Chemical Synthesis Methods

The lysin according to the present invention may be prepared by chemical synthesis techniques.

The lysin or variants, homologues, derivatives, fragments or mimetics thereof may be produced using chemical methods to synthesise the agent in whole or in part. For example, peptides can be synthesised by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Direct synthesis of the lysin or variants, homologues, derivatives, fragments or mimetics thereof can be performed using various solid-phase techniques (Roberge J Y et al (1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences comprising the agent or any part thereof, may be altered during direct synthesis and/or combined using chemical methods with a sequence from other subunits, or any part thereof, to produce a variant agent.

In an alternative embodiment of the invention, the coding sequence of the lysin or variants, homologues, derivatives, fragments or mimetics thereof may be synthesised, in whole or in part, using chemical methods well known in the art (see Caruthers M H et al (1980) Nuc Acids Res Symp Ser 215-23, Horn T et al (1980) Nuc Acids Res Symp Ser 225-232).

Mimetic

As used herein, the term "mimetic" relates to any chemical which includes, but is not limited to, a peptide, polypeptide, antibody or other organic chemical which has the same qualitative activity or effect as a reference agent. That is a mimetic may be a functional equivalent to a known agent.

Chemical Derivative

The term "derivative" or "derivatised" as used herein includes chemical modification of an agent. Illustrative of such chemical modifications would be replacement of hydrogen by a halo group, an alkyl group, an acyl group or an amino group.

Chemical Modification

In one embodiment of the present invention, the lysin may be a chemically modified lysin.

The chemical modification of a lysin may either enhance or reduce hydrogen bonding interaction, charge interaction, hydrophobic interaction, Van Der Waals interaction or dipole interaction between the agent and the target.

In one aspect, the identified lysin may act as a model (for example, a template) for the development of other compounds.

Vector

In one embodiment of the present invention, a lysin according to the present invention may be administered directly to a subject.

In another embodiment of the present invention, a vector comprising a nucleic acid comprising a nucleotide sequence encoding a lysin of the present invention is administered to a subject.

Preferably the recombinant agent is prepared and/or delivered to a target site using a genetic vector.

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences of the present invention and/or expressing the proteins of the invention encoded by the nucleotide sequences of the present invention. Examples of vectors used in recombinant DNA techniques include but are not limited to plasmids, chromosomes, artificial chromosomes or viruses.

The term "vector" includes expression vectors and/or transformation vectors.

The term "expression vector" means a construct capable of in vivo or in vitro/ex vivo expression.

The term "transformation vector" means a construct capable of being transferred from one species to another.

Naked DNA

The vectors comprising nucleotide sequences encoding a lysin of the present invention may be administered directly as "a naked nucleic acid construct", preferably further comprising flanking sequences homologous to the host cell genome.

As used herein, the term "naked DNA" refers to a plasmid comprising a nucleotide sequences encoding an agent of the present invention together with a short promoter region to control its production. It is called "naked" DNA because the plasmids are not carried in any delivery vehicle. When such a DNA plasmid enters a host cell, such as a eukaryotic or prokaryotic cell, the proteins it encodes (such as an agent of the present invention) are transcribed and translated within the cell.

Non-Viral Delivery

Alternatively, the vectors comprising nucleotide sequences of the present invention or a lysin of the present invention may be introduced into suitable host cells using a variety of non-viral techniques known in the art, such as transfection, transformation, electroporation and biolistic transformation.

As used herein, the term "transfection" refers to a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) Nature Biotechnology 1996 14; 556), multivalent cations such as spermine, cationic lipids or polylysine, 1,2,-bis(oleoyloxy)-3-(trimethylammonio) propane (DOTAP)-cholesterol complexes (Wolff and Trubetskoy 1998 Nature Biotechnology 16: 421) and combinations thereof.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Viral Vectors

Alternatively, the vectors comprising an agent of the present invention or nucleotide sequences of the present invention may be introduced into suitable host cells using a variety of viral techniques which are known in the art, such as for example infection with recombinant viral vectors such as retroviruses, herpes simplex viruses and adenoviruses.

Preferably the vector is a recombinant viral vectors. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors (see Kestler et al 1999 Human Gene Ther 10(10): 1619-32). In the case of viral vectors, delivery of the nucleic acid comprising a nucleotide sequence encoding the agent of the present invention is mediated by viral infection of a target cell.

Targeted Vector

The term "targeted vector" refers to a vector whose ability to infect/transfect/transduce a cell or to be expressed in a host and/or target cell is restricted to certain cell types within the host organism, usually cells having a common or similar phenotype.

Replication Vectors

The nucleic acid comprising nucleotide sequences encoding a lysin of the present invention may be incorporated into a recombinant replicable vector. The vector may be used to replicate the nucleotide sequence in a compatible host cell. Thus in one embodiment of the present invention, the invention provides a method of making nucleic acids comprising the nucleotide sequences of the present invention by introducing a nucleic acid comprising the nucleotide sequence of the present invention into a replicable vector, introducing the vector into a compatible host cell, and growing the host cell under conditions which bring about replication of the vector. The vector may be recovered from the host cell.

Expression Vector

Preferably, a lysin of the present invention or a nucleotide sequence of present invention which is inserted into a vector is operably linked to a control sequence that is capable of providing for the expression of the coding sequence by the host cell, i.e. the vector is an expression vector. The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences. The term "regulatory sequences" include promoters and enhancers and other expression regulation signals.

Enhanced expression of the polynucleotide encoding the polypeptide of the invention may also be achieved by the selection of heterologous regulatory regions, e.g. promoter, secretion leader and terminator regions, which served to increase expression and, if desired, secretion levels of the protein of interest from the chosen expression host and/or to provide for the inducible control of the expression of the polypeptide of the present invention.

A lysin of the present invention produced by a host recombinant cell may be secreted or may be contained intracellularly depending on the sequence and/or the vector used. As will be understood by those of skill in the art, expression vectors containing an agent of the present invention coding sequences can be designed with signal sequences which direct secretion of the lysin of the present invention coding sequences through a particular prokaryotic or eukaryotic cell membrane.

Promoters

Aside from the promoter native to the gene of the polypeptide of the invention, other promoters may be used to direct expression of the polypeptide of the invention.

The promoter may be selected for its efficiency in directing the expression of the polypeptide of the invention in the desired expression host.

In another embodiment, a constitutive promoter may be selected to direct the expression of the desired polypeptide of the invention. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

Expression in Vitro

The vectors of the present invention may be transformed or transfected into a suitable host cell and/or a target cell as described below to provide for expression of a lysin the present invention. This process may comprise culturing a host cell and/or target cell transformed with an expression vector under conditions to provide for expression by the vector of a coding sequence encoding a lysin of the present invention and optionally recovering the expressed agent of the present invention. The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. The expression of an agent of the present invention or target of the present invention may be constitutive such that they are continually produced, or inducible, requiring a stimulus to initiate expression. In the case of inducible expression, production of an agent of the present invention or a target can be initiated when required by, for example, addition of an inducer substance to the culture medium, for example dexamethasone or IPTG.

Secretion Leader Sequence

Often, it is desirable for the polypeptide of the invention to be secreted from the expression host into the culture medium from where the polypeptide of the invention may be more easily recovered. According to the present invention, the polypeptide of the invention's native secretion leader sequence may be used to effect the secretion of the expressed polypeptide of the invention. However, an increase in the expression of the polypeptide of the invention sometimes results in the production of the protein in levels beyond that which the expression host is capable of processing and secreting, creating a bottleneck such that the protein product accumulates within the cell. Accordingly, the present invention also provides heterologous leader sequences to provide for the most efficient secretion of the polypeptide of the invention from the chosen expression host.

According to the present invention, the secretion leader may be selected on the basis of the desired expression host. A heterologous secretion leader may be chosen which is homologous to the other regulatory regions of the expression construct. For example, the leader of the highly secreted amyloglucosidase (AG) protein may be used in combination with the amyloglucosidase (AG) promoter itself, as well as in combination with other promoters. Hybrid signal sequences may also be used with the context of the present invention.

Examples of preferred heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces* and *Kluyveromyces*) or the α-amylase gene (*Bacillus*).

Fusion Proteins

The lysin of the present invention may be expressed as a fusion protein to aid extraction and purification and/or delivery of the lysin of the present invention to a subject. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the lysin.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Host Cells

A wide variety of host cells can be employed for expression of the nucleotide sequences encoding the lysin of the present invention. These cells may be both prokaryotic and eukaryotic host cells. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides. Suitable host cells include bacteria such as *Escherichia coli, Lactobacillus* spp., *Bacillus* spp., and *Lactococcus* spp, yeast, filamentous fungi, insect cells, mammalian cells, typically immortalised, e.g., mouse, CHO, human and monkey cell lines and derivatives thereof.

The vectors may be for example, plasmid, virus or phage vectors provided with an origin of replication, optionally a promoter for the expression of the said polynucleotide and optionally a regulator of the promoter. The vectors may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in fungi), the ampicillin resistance gene (*E. coli*), the neomycin resistance gene (*Bacillus*) and the *E. coli* uidA gene, coding for β-glucuronidase (GUS). Vectors may be used in vitro, for example for the production of RNA or used to transfect or transform a host cell.

A further embodiment of the invention provides host cells transformed or transfected with a polynucleotide of the invention. Preferably said polynucleotide is carried in a vector for the replication and expression of said polynucleotides. The cells will be chosen to be compatible with the said vector and may for example be prokaryotic (for example bacterial), fungal, yeast or plant cells.

Bacteria from the genera *Bacillus* and *Lactobacillus* are very suitable as heterologous hosts because of their capability to secrete proteins into the culture medium. Other bacteria suitable as hosts are those from the genera *Lactococcus*.

Depending on the nature of the polynucleotide encoding the polypeptide of the invention, and/or the desirability for further processing of the expressed protein, eukaryotic hosts such as yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

A heterologous host may also be chosen wherein the polypeptide of the invention is produced in a form which is substantially free from other lysins. This may be achieved by choosing a host which does not normally produce such agents.

Examples of preferred expression hosts within the scope of the present invention are fungi such as *Aspergillus* species and *Trichoderma* species; bacteria such as *Bacillus* species and *Lactobacillus* species; and yeasts such as *Kluyveromyces* species and *Saccharomyces* species.

Particularly preferred expression hosts may be selected from *Aspergillus niger, Aspergillus niger* var. *tubigenis, Aspergillus niger* var. *awamori, Aspergillus aculeatis, Aspergillus nidulans, Aspergillus oryzae, Trichoderma reesei, Lactobacillus acidophilus, Bacillus subtilis, Bacillus licheniformis, Bacillus amyloliquefaciens, Kluyveromyces lactis* and *Saccharomyces cerevisiae.*

According to the present invention, the production of the polypeptide of the invention can be effected by the culturing of microbial expression hosts, which have been transformed with one or more polynucleotides of the present invention, in a conventional nutrient fermentation medium.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer may be added.

The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating microorganisms.

After fermentation, the cells can be removed from the fermentation broth by means of centrifugation or filtration. After removal of the cells, the variant polypeptide of the invention may then be recovered and, if desired, purified and isolated by conventional means.

Organisms

The term "organism" in relation to the present invention includes any organism that could comprise a nucleic acid comprising a nucleotide sequence coding for a lysin according to the present invention and/or products obtained therefrom, wherein a transcriptional regulatory sequence can allow expression of the nucleotide sequence according to the present invention when present in the organism. Suitable organisms may include a prokaryote, fungus, yeast or a plant. A preferable organism may be a bacterium, preferably of the genus *Lactobacillus*, more preferably *Lactobacillus acidophilus.*

The term "transgenic organism" in relation to the present invention includes any organism that comprises the nucleic acid comprising the nucleotide sequence coding for the protein according to the present invention and/or products obtained therefrom, wherein the transcriptional regulatory sequence can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the desired compound which would be easily retrievable from, the cell or organism.

Transformation of Host Cells/Host Organisms

As indicated earlier, the host organism can be a prokaryotic or a eukaryotic organism. Examples of suitable prokaryotic hosts include *E. coli, Bacillus subtilis* or *Lactobacillus acidophilus*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae.*

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol. 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

Reporters

A wide variety of reporters may be used in the detection methods and assay methods (as well as screens) of the present invention with preferred reporters providing conveniently detectable signals (e.g. by spectroscopy). By way of example, a reporter gene may encode an enzyme which catalyses a reaction which alters light absorption properties.

Examples of reporter molecules include but are not limited to β-galactosidase, invertase, green fluorescent protein, luciferase, chloramphenicol, acetyltransferase, β-glucuronidase, exo-glucanase and glucoamylase. Alternatively, radiolabelled or fluorescent tag-labelled nucleotides can be incorporated into nascent transcripts which are then identified when bound to oligonucleotide probes.

In the detection method of the present invention, the lysin or a portion thereof may be bonded by genetic, translational fusions directly or indirectly to a reporter, suitably a fluorescent protein (such as green fluorescent protein for example).

A variety of protocols for detecting and measuring the expression of a protein, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on polypeptides is preferred, but a competitive binding assay may be employed. These and other assays are described, among other places, in Hampton R et al (1990, Serological Methods, A Laboratory Manual, APS Press, St Paul Minn.) and Maddox D E et al (1983, J Exp Med 15 8:121 1).

The production of the reporter molecule may be measured by the enzymatic activity of the reporter gene product, such as β-galactosidase.

A wide variety of labels and conjugation techniques are known by those skilled in the art and can be used in various nucleic and amino acid assays. Means for producing labelled hybridisation or PCR probes for detecting the target polynucleotide sequences include oligolabelling, nick translation, end-labelling or PCR amplification using a labelled nucleotide. Alternatively, the coding sequence, or any portion of it, may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567.

Additional methods to quantify the expression of a particular molecule include radiolabeling (Melby P C et al 1993 J Immunol Methods 159:235-44) or biotinylating (Duplaa C et al 1993 Anal Biochem 229-36) nucleotides, coamplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the nucleotide sequence is inserted within a marker gene sequence, recombinant cells containing the same may be identified by the absence of marker gene function. Alternatively, a marker gene can be placed in tandem with a target coding sequence under the control of a single promoter. Expression of the marker gene in response to induction or selection usually indicates expression of the target as well.

Alternatively, host cells which contain the coding sequence for the target and express the target coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

Screens

Any one or more of appropriate targets—such as a sample comprising one or more pathogenic *Clostridium* bacterium, in particular a *C. perfringens* bacterium—may be used for identifying a lysin according to the present invention, in any of a variety of drug screening techniques. The target employed in such a test may be free in solution, affixed to a solid support, borne on a cell surface, or located intracellularly. The target may even be within an animal model, wherein said target may be an exogenous target or an introduced target. The animal model will be a non-human animal model. The abolition of target activity or the formation of binding complexes between the target and the lysin being tested may be measured.

It is expected that the assay methods of the present invention will be suitable for both small and large-scale screening of test compounds as well as in quantitative assays.

In a preferred aspect, the screen of the present invention comprises at least the following steps (which need not be in this same consecutive order): (a) conducting an in vitro screen to determine whether a candidate lysin has the relevant activity (such as the ability to lyse one or more pathogenic *Clostridium* bacteria, preferably *C. perfringens* bacteria); and (b) conducting an in vivo screen with said candidate lysin (e.g. using a functional animal model). Typically, if said candidate agent passes screen (a) then screen (c) is performed.

Diagnostics

The present invention also provides a diagnostic composition or kit for the detection of a target, namely a pathogenic *Clostridium* bacterium, particularly a *C. perfringens* bacterium. In this respect, the composition or kit will comprise a diagnostic marker based on the lysin according to the present invention that is capable of indicating the presence of one or more—or even the absence of one or more—*Clostridium* bacteria, particularly a *C. perfringens* bacterium, in a test sample.

Suitably, the test sample may be a foodstuff, digesta or a test sample obtained from the intestinal tract of a subject, for example.

The diagnostic composition or kit may be used for the detection of a target, namely a pathogenic *Clostridium* bacterium, particularly a *C. perfringens* bacterium, in, for example, a food stuff, digesta or the like.

The diagnostic composition or kit may be used for the diagnosis of disorders caused by the presence of pathogenic *Clostridium* bacteria, particularly *C. perfringens*, such as necrotic enteritis, food poisoning or gangrene for example.

Such a diagnostic assay may be tailored to evaluate the efficacy of a particular treatment regime or of a particular lysin and may be used in animal studies, in clinical trials, or in monitoring the treatment of a subject. In order to provide a basis for the diagnosis of disease, a normal or standard profile should be established. This is accomplished by combining body fluids or cell extracts or other samples taken from normal (i.e. non-infected) subjects, either animal or human, with the lysin of the present invention. If disease is established, a therapeutic agent, i.e. a lysin according to the present invention and/or a host transformed with a nucleotide sequence encoding a lysin according to the present invention, is administered, and treatment profile or values may be generated. Finally, the assay may be repeated on a regular basis to evaluate whether the values progress toward or return to the normal or standard pattern, i.e. whether the amount of bacteria in a sample, such as in the gut of poultry during treatment thereof, is reduced and/or eradicated. Successive treatment profiles may be used to show the efficacy of treatment over a period of several days or several months.

Diagnostic Testing

In order to provide a basis for the diagnosis of disease, normal or standard values of the amount of pathogenic *Clostridium* bacteria, in particular *C. perfringens* bacteria, in a sample should be established. For example, a certain level of said bacteria in the intestinal tract of a subject may not be necessarily harmful to the individual. Only when the bacterial numbers increase above a threshold level, may harmful effects be observed and a disease state established. Thus, the diagnostic test may be able to identify the presence of pathogenic *Clostridium* bacteria, in particular *C. perfringens*, in a sample, but may also be able to quantify the level of infection. The amount of bacterium in a sample may be quantified by comparing it to a dilution series of positive controls where a known amount of bacteria are added.

Probes

Another aspect of the subject invention is the provision of nucleic acid hybridisation or PCR probes which are capable of detecting (especially those that are capable of selectively selecting) polynucleotide sequences, including genomic sequences, encoding a nucleotide sequence encoding a lysin according to the present invention, or closely related molecules, such as alleles. The specificity of the probe, i.e., whether it is derived from a highly conserved, conserved or non-conserved region or domain, and the stringency of the hybridisation or amplification (high, intermediate or low) will determine whether the probe identifies only naturally occurring nucleotide sequences encoding a lysin of the present invention, or related sequences. Probes for the detection of related nucleic acid sequences are selected from conserved or highly conserved nucleotide regions of target family members and such probes may be used in a pool of degenerate probes. For the detection of identical nucleic acid sequences, or where maximum specificity is desired, nucleic acid probes are selected from the non-conserved nucleotide regions or unique regions of the target polynucleotides. As used herein, the term "non-conserved nucleotide region" refers to a nucleotide region that is unique to a lysin coding sequence disclosed herein and does not occur in related family members.

PCR as described in U.S. Pat. Nos. 4,683,195, 4,800,195 and 4,965,188 provides additional uses for oligonucleotides based upon the nucleotide sequences. Such oligomers are generally chemically synthesised, but they may be generated enzymatically or produced from a recombinant source. Oligomers generally comprise two nucleotide sequences, one with sense orientation (5'->3') and one with antisense (3'<-5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for a lysin according to the present invention can also be used to generate hybridisation probes as previously described, for mapping the endogenous genomic sequence. The sequence may be mapped to a particular chromosome or to a specific region of the chromosome using well known techniques.

These include in situ hybridisation to chromosomal spreads (Verma et al (1988) Human Chromosomes: A Manual of Basic Techniques, Pergamon Press, New York City), flow-sorted chromosomal preparations, or artificial chromosome constructions such as YACs, bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome has been crudely localised by genetic linkage to a particular genomic region any sequences mapping to that area may represent associated or regulatory genes for further investigation. The nucleotide sequence of the subject invention may also be used to detect differences in the chromosomal location due to translocation, inversion, etc. between normal, carrier or affected individuals.

Uses

In a general sense, a lysin according to the present invention and/or the host transformed with a nucleotide sequence encoding a lysin according to the present invention may be used in the manufacture of a medicament of the treatment of a disorder associated with the presence of pathogenic *Clostridium* bacteria, in particular *C. perfringens* bacteria.

The lysin according to the present invention and/or the host transformed with a nucleotide sequence encoding a lysin according to the present invention may be used to test for and/or destroy pathogenic *Clostridium* bacteria, in particular *C. perfringens.*

In particular, a lysin according to the present invention and/or a host transformed with a nucleic acid comprising a nucleotide sequence encoding a lysin according to the present invention may be used in animal feed or as an animal feed supplement to reduce the amount of pathogenic *Clostridium* bacteria, in particular *C. perfringens*, in the intestinal tract of the animal. Thus, disorders such as reduced weight gain and necrotic enteritis caused by the presence of pathogenic *Clostridium* bacteria, in particular *C. perfringens*, may be prevented and/or treated.

A lysin according to the present invention and/or a host transformed with a nucleic acid comprising a nucleotide sequence encoding a lysin according to the present invention may also be used to prevent and/or treat gangrene and other diseases associated with the presence of pathogenic *Clostridium* bacteria, in particular *C. perfringens.*

In addition or alternatively thereto, a lysin according to the present invention and/or a host transformed with a nucleic acid comprising a nucleotide sequence encoding a lysin according to the present invention may be used in an assay to test for and detect the causative agent in a food poisoning outbreak and/or to prevent or treat food poisoning in an individual and/or as a diagnostic for research purposes.

Preparation of Foodstuffs

A lysin according to the present invention and/or a host transformed with a nucleic acid comprising a nucleotide sequence encoding a lysin according to the present invention may be used in foodstuffs including animal feed.

In one embodiment, the food and/or feed supplement of the present invention may be prepared by mixing the lysin according to the present invention and/or the host transformed with a nucleic acid comprising a nucleotide sequence encoding a lysin according to the present invention directly with a food and/or feed supplement. By way of example, the lysin according to the present invention and/or the host transformed with a nucleic acid comprising a nucleotide sequence encoding a lysin according to the present invention may be contacted (for example, by spraying) onto a cereal-based food and/or feed supplement such as milled wheat, maize or soya flour.

It is also possible to incorporate the lysin according to the present invention and/or the host transformed with a nucleic acid comprising a nucleotide sequence encoding a lysin according to the present invention into a second (and different) food and/or feed or drinking water which is then added to the food and/or feed supplement of the present invention. Accordingly, it is not essential that the lysin according to the present invention and/or the host transformed with a nucleic acid comprising a nucleotide sequence encoding a lysin according to the present invention is incorporated into the cereal-based food and/or feed supplement itself, although such incorporation forms a particularly preferred aspect of the present invention.

In one embodiment of the present invention, the food and/or feed supplement may be combined with other food and/or feed components to produce a cereal-based food and/or feed. Such other food and/or feed components may include one or more other (preferably thermostable) enzyme supplements, vitamin food and/or feed supplements, mineral food and/or feed supplements and amino acid food and/or feed supplements. The resulting (combined) food and/or feed supplement comprising possibly several different types of compounds can then be mixed in an appropriate amount with the other food and/or feed components such as cereal and protein supplements to form a human food and/or an animal feed.

The invention will now be further described by way of example in which reference will be made to the following Figures:

FIGURES

FIG. 1 which shows a nucleotide sequence;

FIG. 2 which shows an amino acid sequence;

FIG. 3 which shows a genomic map;

FIG. 4 which shows a graph; and

FIG. 5 which shows a graph

In more detail:

FIG. 1 shows a nucleotide sequence (SEQ ID No. 1) encoding a lysin according to the present invention;

FIG. 2 shows an amino acid sequence (SEQ ID No. 2) of a lysin according to the present invention;

EXAMPLES

Example 1

Figure 3:
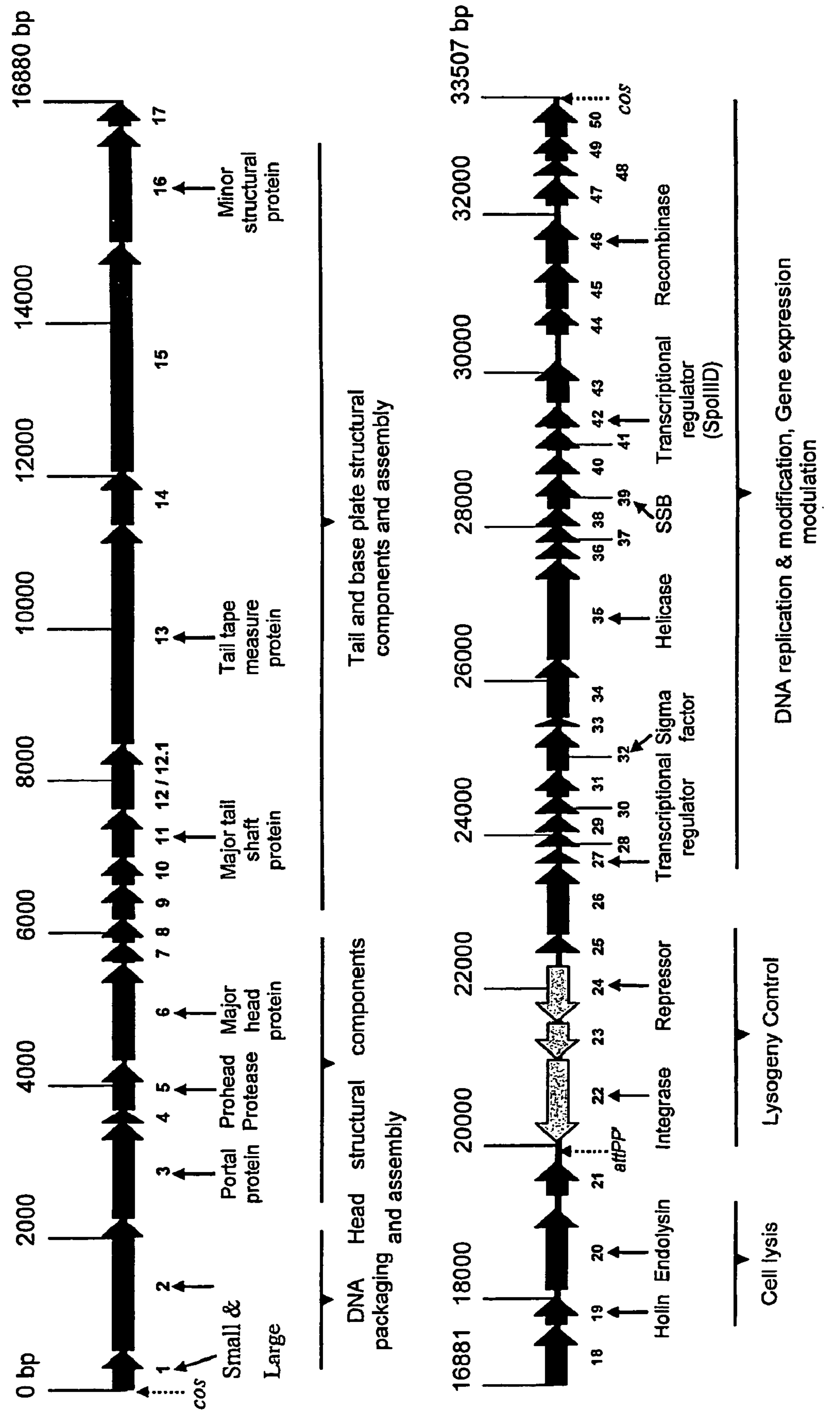
FIG. 3 shows a genomic map in respect of bacteriophage (ϕ3626) from *Clostridium perfringens;*

Isolation and Purification of Bacteriophages from *C. perfringens*

Method: Fifty-one clostridial strains isolated from various sources were screened for lysogeny by the UV-irradiation technique as described in Loessner et al (1990 Appl. Environ. Microbiol, 56, 1912-8). Exponentially growing clostridia (10 ml) were exposed to UV-light (254 nm, 0.0132 J $cm^{-2}$) for 5 min. After a 3 h incubation (37° C.) in the dark the cultures were centrifuged (10 min 8000 g) and sterile filtered. Phage activity was tested by the spot on the lawn method against all *C. perfringens* strains.

The soft agar layer technique described in Adams (1959 Methods of study of bacterial viruses p 443-457 Bacteriophages, Intersciences Publishers Inc. NY) was used for the purification and propagation of the phages. Dilutions of the supernatants displaying lytic activity were added to 3.5 ml of molten soft agar inoculated with 0.1 ml of exponential growing culture of the appropriate propagation strain. The soft agar was poured on TY plates and incubated overnight. Single, well-isolated plaques were picked with a sterile Pasteur pipette and placed into 0.45 ml of TY medium. After a 4 h incubation at 4° C. the phage-containing solution was sterile filtered and used for a second round of purification.

For the isolation of DNA from bacteriophages a high-titre stock ($10^9$ pfu/ml) was essential. The phages were propagated to high titres by liquid cultures. To a culture of the appropriate host ($OD_{600\ nm}$ of 0.1) a phage solution was added at a multiplicity of infection of about 1. The growth of the infected culture was monitored photometrically and the phages were harvested after removal of cellular debris by centrifugation (10000 g for 10 min) and sterile-filtration of the culture supernatant.

Purification of the phages from the high titre stocks necessary for further molecular work has been described in Zink et al (1992 Appl. Environ. Microbiol. 58, 296-302). Briefly, the phages were purified and concentrated by polyethylene glycol 8000 precipitation, stepped CsCl density gradient centrifugation and dialysis (see, for example, Sambrook et al Molecular Cloning: a laboratory manual, $2^{nd}$ ed. Cold Spring Harbor Laboratory Press, Cold Spring Harbor, N.Y.). The putative phage particles were examined by electron microscopy (EM).

Results: With strains ATCC3626 and NCTC8533, the observed lytic activity of UV-induced sterile culture supernatant was due to the presence of bacteriophages, which was confirmed by EM. The phages were of the Siphoviridae type, and were named ϕ3626 and ϕ8533. The optimal propagation host for the two phages were determined to be NCTC3110 and strain ATCC3628, respectively.

Example 2

Determination of the Lytic Range of the Bacteriophages

Method: The ability of the two phages to lyse *C. perfringens* strains was tested by the drop-on-the-lawn technique. Ten μl of phage stocks ($10^7$ pfu/ml) were placed on the plates inoculated with *C. perfringens* strains. The lytic activity was observed by formation of plaques in the lawns of the bacteria after overnight incubation.

Results: Phage ϕ3626 was lytic against 11 strains of the 51 *C. perfringens* strains (21.6%) while phage ϕ8533 was able to lyse 4 strains (7.8%).

Example 3

Sequencing and Analysis of Genomic DNA of Bacteriophage ϕ3626 from *C. perfringens*

Method: The genomic DNA of ϕ3626 was obtained using the standard method for the extraction of bacteriophage λ DNA (see Sambrook et al supra). The construction of genomic libraries of bacteriophage ϕ3626 was performed as detailed in Loessner et al (2000 Mol. Microbiol 35, 324-40). A time-limited digest of the DNA with Tsp509I (New England Biolabs) and full digests using HindIII (MBI Fermentas) and TaqI (Roche) was performed. Fragments of the desired length (1-2 kbp) were recovered from an agarose gel and ligated in vector pBluescript (Stratagene). The ligation products were electroporated into *E. coli* DH5αMCR. Blue-white screening on Xgal-containing agar plates was used for the identification of insert-bearing transformants. Plasmids were isolated from small-scale cultures (Qiaprep Miniprep Kit; Qiagen) and digested with Paul (MBI). Fifty-eight clones carrying different inserts—varying in the length between 1-2 kbp—were identified by the restriction pattern in an agarose gel. These clones were used for sequencing using fluorescent-labelled (IRD-800 LI-COR) standard primers being complementary to sequences flanking the multiple cloning site of pBluescript. The sequencing was performed using a heat-stable polymerase (SequiTherm EXCEL II DNA Sequencing Kit-LC; Epicentre Technologies) on an automated DNA sequencer (4200 $IR^2$; LI-COR).

The obtained sequences were aligned using the software DNASIS version 2.10 (Hitachi). Contigs derived from that alignment were used for the design of specific primer to close the gaps. Remaining gaps were closed by primer walking on ϕ3626 DNA until a distinct chain termination was observed at the cos-site. The genome sequence was finalised by the determination of the core sequence of the cos-site by PCR on the DNA of the lysogenic host using primer complementary to sequences upstream and downstream of the cos-site. PCR products and the DNA stretches from the primer walking approach were sequenced by using the dyed terminator technique on a ABI 373A automated DNA sequencer.

DNASIS/PROSIS (Hitachi) and the Husar Analysis Package, including the GCG package (http://genius.embnet.dkfz-heidelberg.de; Biocomputing Service Group at the German Cancer Research Center, DKFZ) were used for analysis of the nucleotide and amino acid sequences. The BLAST algorithm taught in Altschul et al (1990 J. Mol. Biol 215, 403-10) was used for the homology searches on the databases available through the National Center for Biotechnology Information (http://www.ncbi.nlm.nih.gov) or the Biocomputing Service Group.

Results: The ϕ3626 genome has a length of 33507 bp with 3'-protruding, single-stranded cohesive ends with a length of 9 nucleotides. The average molar GC content is 28.4 mol %. Bioinformatic analysis of the ϕ3626 genome revealed the existence of 50 putative protein coding regions covering 94.1% of the sequence.

The protein coding regions the genome of ϕ3626 can be organised into three major functional clusters, apparent by the direction of the ORFs. (see FIG. 3). The first cluster from the cos-site at coordinates 1 to 19804, transcribed rightward in the genomic map (FIG. 3), represents genes encoding structural proteins and the lysis system. These genes can be summarised as 'late genes'. The second cluster is located from bp 19805-23645 and encodes products responsible for the control of lysogeny including the att-site, an integrase, the repressor and a putative cro-repressor. The last cluster—reaching from nucleotide 23680 to 33507—includes ORFs that are solely directed in the rightward direction (see FIG. 3). Their putative products are responsible for the replication, recombination, modification of the phage DNA and represent 'early' genes.

Example 3

Sequence Determination of Lysin Gene

Method: Comparison with other bacteriophages (ϕ105, Sfi21, ϕadh, ϕSLT, ϕPVL) revealed a similar organisation of the genome of ϕ3626. Typically, the endolysin was located upstream of the lysogeny control region whose ORFs are usually directed in the opposite direction (see FIG. 3). The product of ORF19 displayed similarities (50% over 105 amino acids) with the probable holin from *Bacillus subtilis* phage ϕ105 (Kobayashi, K et. al., unpublished, Accession number: AB016282). Using bioinformatic analysis implementing TmHMM, as described in Sonnhammer et al (1998 Proc. Int. Conf. Intell. Syst. Mol. Biol., 6:175-182) it was established there was a high probability that the putative protein does have two transmembrane helix regions. Thus, it was tentatively assumed that ORF19 encoded a holin of ϕ3626.

In tailed bacteriophages, the endolysin gene can be located downstream of the gene encoding the holin (see Wang et al (2000 Ann. Rev. Microbiol. 54:799:825). A homology search using BLASTP2 revealed a strong similarity (72-75% over 265-346 amino acids) of the deduced gene product of ORF20 with hypothetical proteins of *C. perfringens* with unknown function (see Garnier et al 1988 Plasmid 19:135-50; Lyristis et al 1994 Mol. Microbiol 12:761-77; Shimizu et al 1994 J. Bacteriol. 176: 1616-23). Within the amino terminus, it displayed similarities to N-acetylmuramoyl-L-alanine amidases from different sources (*Bacillus subtilis* autolysin, *Bacillus cereus* bacteriophage 12862 endolysin, CwlV from *Paenibacillus polymyxa*, with similarities from 43-45% over 163-166 amino acids) (see Ishikawa et al 1999 Mol. Gen. Genet 262: 738-48; Kunst et al 1997 Nature 390; 249-56; and Loessner et al 1997 J. Bacteriol 179: 2845-51). A Hidden Markov Model (HMM) scan using the PFAM database (see Durbin et al 1998 Biological Sequence Analysis: Probabilistic Models of Proteins and Nucleic Acids, Cambridge Uni. Press) also suggested also the existence of a putative N-acetylmuramoyl-L-alanine amidase domain.

Results: ORF20 was identified as the endolysin encoding gene ply3626 and was found to be directly downstream of the gene encoding the holin. The probability that the enzyme possessed an amidase domain within the amino terminus also indicated that ORF20 was an endolysin. No known function is indicated for the carboxy terminus of the endolysin, but based on the finding that many endolysins display a modular organization (see Garcia et al 1990 Gene 86:81-8), it is assumed that a possible cell wall binding domain might be located within the carboxy terminus of ply3626.

Example 4

Expression of ply3626 in *E. coli*

Based on the bioinformatic analysis, primers were designed for the amplification of ply3626 using PCR. The primers were designed to be complementary to the ends of the gene and to possess restriction sites upstream and downstream of the gene to allow directed cloning into the expression vector pQE30 (Qiagen). The PCR product was purified, digested with the appropriate restriction endonuclease and ligated in the prepared vector. The ligation products were transformed by electroporation into *E. coli* JM109 that have previously been prepared by transformation with plasmid pACYC-IRL10 kindly provided by Zdanovsky et al (2000 App. Environ Microbiol 166: 3166-73). The pACYC-IRL10 provided *E. coli* with the genes for tRNAs (ileX, argU and leuW) rarely used in *E. coli* but frequently used in Clostridia.

The *E. coli* transformed with the vector encoding the endolysin were grown at room temperature (22° C.), producing the endolysin solely by the background expression of the vector system. This was found to prevent the formation of inclusion bodies, which was observed by the use of IPTG for induction. After 16 h the cells were harvested by centrifugation (8000 g, 15 min). The pellets were resuspended in PBS buffer and raw extracts (RE) of the cells were prepared by using a French press cell at 40000 kPa The RE was centrifuged for 30 min at 35000 g and sterile filtered. The activity of the enzyme was shown by a lysis assay on *C. perfringens* NCTC3110 cells.

The endolysin could also be purified, by using the HIS-tag fused to the endolysin by the expression vector pQE30. The purified endolysin displayed the same lytic activity as the endolysin in the raw extract.

Example 5

Lysis Assay with ply3626 Produced by Recombinant *E. coli* on *C. perfringens*

Figure 4:
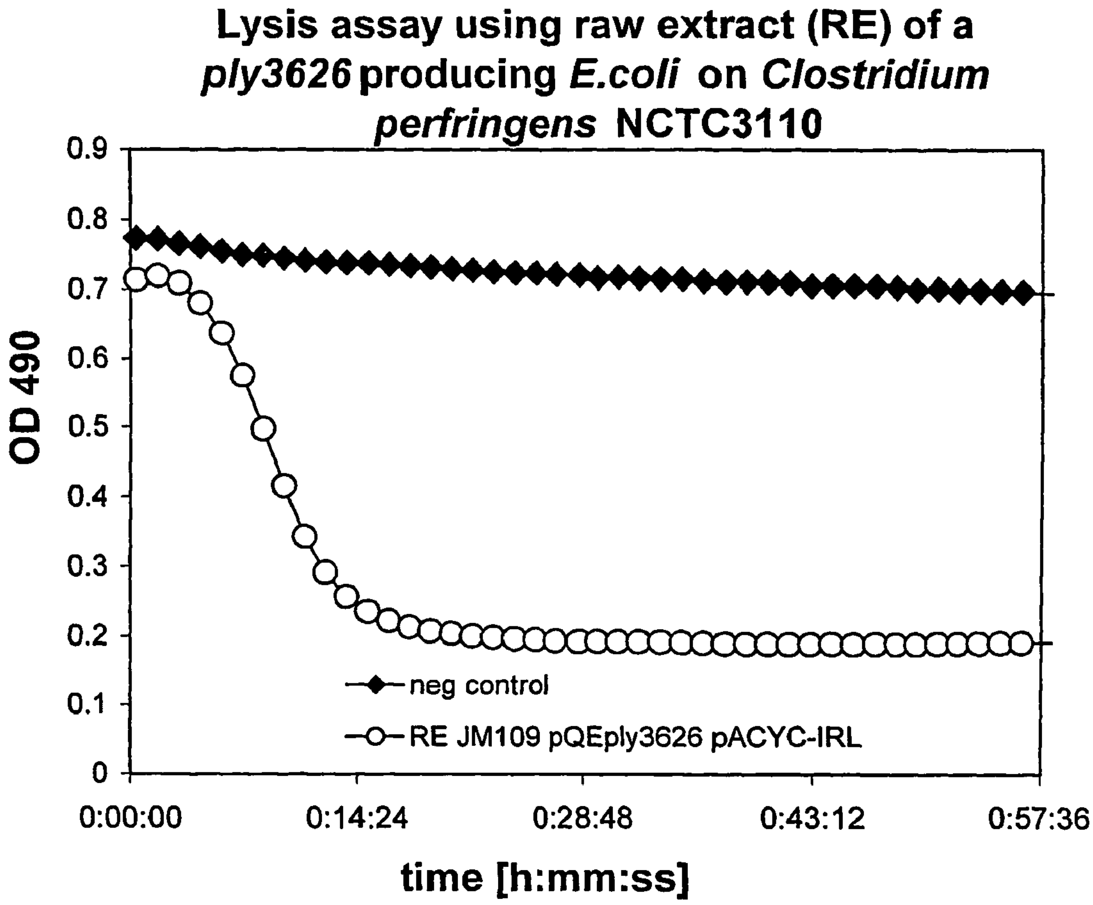
FIG. 4 shows a graph of the lysis of *C. perfringens* strain NCTC3110 in a medium by use of a raw extract (RE) of a ϕ3626 lysin producing *E. coli*.

For a photometric assay on lytic activity, *C. perfringens* NCTC3110 was used as a substrate for ply3626. The bacteria were grown overnight (500 ml), harvested by centrifugation (8000 g for 15 min) and resuspended in PBS buffer (5 ml). The cells were stored until usage at −20° C. For the lysis assay the cells were diluted to an optical density of 0.7-0.8 at 490 m in PBS buffer. To 180 μl of this substrate 20 μl of the raw extract of the recombinant *E. coli* producing the endolysin were added and the changes in optical density was measured over time. As a negative control, a raw extract of *E. coli* was used bearing the vector with a 3' truncated ply3626 gene. A visible reduction in the optical density, due to the disruption of the cell walls of the substrate was measured for the RE containing the endolysin ply3626 (see FIG. 4), in comparison with the negative control.

Example 6

Substrate Specificity

Method: For the determination of the substrate specificity of the lysin obtained from *C. perfringens*, the lysis assay with ply3626 was performed with various bacteria 109 strains of 49 different bacterial species were screened for sensitivity against Ply3626. The bacteria were grown under standard conditions, harvested by centrifugation and the pellets were resuspended in PBS. These stocks were stored at −20° C. until usage. The cells were diluted to obtain an optical density of 0.5-0.9 (at 490 nm) and 180 μl of the diluted cell suspension was used as a substrate for the lysis assay by adding 20 μl of the Ply3626 containing raw extract of the recombinant *E. coli.*

A sigmoid reduction of optical density was interpreted as sensitivity against Ply3626 in comparison with the negative control. In the case where no reduction was detectable it was considered as non-sensitive.

A list of the various bacteria assayed is presented in Tables 1 and 2 below (wherein WS means Weihenstephan Culture Collection of Microorganisms; ATCC means American Type Culture Collection, Rockville, USA; and NCTC means National Collection of Type Cultures, PHLS, London:

TABLE 1 strains obtained from culture collections

| Bacterial species | WS number | official number | sensitivity |
|---|---|---|---|
| *Bacillus cereus* | WS 1537 | DSM 31 | no |
| *Bacillus megaterium* | WS 1539 | DSM 32 | no |
| *Bacillus polymyxa* | WS 1538 | DSM 36 | no |
| *Bacillus subtilis* | WS 1525 | DSM 10 | no |
| *Bacillus thuringiensis* | WS 2734 | DSM 2046 | no |
| *Bifidobacterium gallicum* | WS 3390 | DSM 20093 | no |
| *Bifidobacterium gallinarum* | WS 3410 | DSM 20670 | no |
| *Bifidobacterium ruminantium* | WS 3381 | DSM 6489 | no |
| *Brochothrix thermosphacta* | WS 2021 | DSM 20171 | no |
| *Campylobacter jejuni* | WS 3510 | DSM 4688 | no |

TABLE 1-continued strains obtained from culture collections

| Bacterial species | WS number | official number | sensitivity |
|---|---|---|---|
| *Clostridium absonum* | WS 3511 | DSM 599 | no |
| *Clostridium barati* | WS 3512 | DSM 601 | no |
| *Clostridium fallax* | WS 3514 | DSM 2631 | yes |
| *Clostridium novyi* | WS 3515 | DSM 5566 | no |
| *Clostridium tetani* | WS 3516 | DSM 11744 | no |
| *Clostridium beijerinckii* | WS 2190 | ATCC 6015 | no |
| *Clostridium bifermentans* | WS 2189 | ATCC 19299 | no |
| *Clostridium butyricum* | WS 1619 | DSM 552 | no |
| *Clostridium pasteurianum* | WS 2195 | DSM 525 | no |
| *Clostridium perfringens* | WS2952 | DSM 756$^T$ | yes |
| *Clostridium perfringens* | WS2953 | DSM 798 | yes |
| *Clostridium perfringens* | WS2954 | DSM 2943 | yes |
| *Clostridium perfringens* | WS2964 | NCTC 528 | yes |
| *Clostridium perfringens* | WS2965 | NCTC 3110 | yes |
| *Clostridium perfringens* | WS2966 | NCTC 6719 | yes |
| *Clostridium perfringens* | WS2969 | NCTC 8346 | yes |
| *Clostridium perfringens* | WS2970 | NCTC 8533 | yes |
| *Clostridium perfringens* | WS2971 | NCTC 10240 | yes |
| *Clostridium perfringens* | WS2972 | NCTC 10612 | yes |
| *Clostridium perfringens* | WS2974 | NCTC 10719 | yes |
| *Clostridium perfringens* | WS2975 | NCTC 11144 | yes |
| *Clostridium perfringens* | WS3004 | ATCC 3626 | yes |
| *Clostridium perfringens* | WS3005 | ATCC 3628 | yes |
| *Clostridium sporogenes* | WS 1621 | DSM 633 | no |
| *Clostridium sporogenes* | WS 2186 | DSM 1664 | no |
| *Clostridium sporogenes* | WS 2187 | DSM 795 | no |
| *Clostridium tertium* | WS 2188 | DSM 2485 | no |
| *Clostridium tetanomorphum* | WS 2194 | ATCC 19407 | no |
| *Clostridium tyrobutyricum* | WS 1620 | DSM 663 | no |
| *Clostridium tyrobutyricum* | WS 2191 | ATCC 25755 | no |
| *Enterobacter gallinarum* | WS 3204 | DSM 20628 | no |
| *Enterococcus faecalis* | WS 2331 | DSM 20478 | no |
| *Enterococcus faecium* | WS 1052 | DSM 20477 | no |
| *Escherichia coli* | WS 1322 | DSM 30083 | no |
| *Lactobacillus aviarius subsp. Aviarius* | WS 3206 | DSM 20655 | no |
| *Lactococcus plantarum* | WS 3116 | DSM 20686 | no |
| *Leuconostoc carnosum* | WS 3102 | DSM 5576 | no |
| *Leuconostoc citreum* | WS 3103 | DSM 5577 | no |
| *Leuconostoc mesenteroides* | WS 3105 | DSM 20346 | no |
| *Listeria innocua* | WS 2257 | ATCC 33090 | no |
| *Listeria ivanovii* | WS 2256 | ATCC 19119 | no |
| *Listeria monocytogenes* | WS 2301 | ATCC 15313 | no |
| *Pediococcus pentosaceus* | WS 1038 | DSM 20206 | no |
| *Staphylococcus aureus supsp. Aureus* | WS 2438 | DSM 20231 | no |
| *Staphylococcus epidermidis* | WS 3341 | DSM 20044 | no |
| *Staphylococcus gallinarum* | WS 3287 | DSM 20610 | no |
| *Streptococcus pyogenes* | WS 3154 | DSM 20565 | no |
| *Streptococcus thermophilus* | WS 2786 | DSM 20617 | no |

TABLE 2

Strains from various other sources

| Bacterial species | WS number | official number | sensitivity |
|---|---|---|---|
| *Bacillus weihenstephanensis* | WS 2480 | | no |
| *Clostridium botulinum* | WS 3524 | | no |
| *Clostridium botulinum* | WS 3525 | | no |
| *Clostridium perfringens* | WS2955 | | yes |
| *Clostridium perfringens* | WS2956 | | yes |
| *Clostridium perfringens* | WS2957 | | yes |
| *Clostridium perfringens* | WS2958 | | yes |
| *Clostridium perfringens* | WS2959 | | yes |
| *Clostridium perfringens* | WS2960 | | yes |
| *Clostridium perfringens* | WS2961 | | yes |
| *Clostridium perfringens* | WS2962 | | yes |
| *Clostridium perfringens* | WS2963 | | yes |
| *Clostridium perfringens* | WS2981 | | yes |
| *Clostridium perfringens* | WS2982 | | yes |

TABLE 2-continued

Strains from various other sources

| Bacterial species | WS number | official number | sensitivity |
|---|---|---|---|
| *Clostridium perfringens* | WS2983 | | yes |
| *Clostridium perfringens* | WS2984 | | yes |
| *Clostridium perfringens* | WS2985 | | yes |
| *Clostridium perfringens* | WS2986 | | yes |
| *Clostridium perfringens* | WS2987 | | yes |
| *Clostridium perfringens* | WS2988 | | yes |
| *Clostridium perfringens* | WS2989 | | yes |
| *Clostridium perfringens* | WS2990 | | yes |
| *Clostridium perfringens* | WS2991 | | yes |
| *Clostridium perfringens* | WS2992 | | yes |
| *Clostridium perfringens* | WS2993 | | yes |
| *Clostridium perfringens* | WS2994 | | yes |
| *Clostridium perfringens* | WS2995 | | yes |
| *Clostridium perfringens* | WS2996 | | yes |
| *Clostridium perfringens* | WS2997 | | yes |
| *Clostridium perfringens* | WS2998 | | yes |
| *Clostridium perfringens* | WS2999 | | yes |
| *Clostridium perfringens* | WS3000 | | yes |
| *Clostridium perfringens* | WS3001 | | yes |
| *Clostridium perfringens* | WS3002 | | yes |
| *Clostridium perfringens* | WS3006 | | yes |
| *Clostridium perfringens* | WS3007 | | yes |
| *Clostridium perfringens* | WS3008 | | yes |
| *Clostridium tyrobutyricum* | WS 2761 | | no |
| *Clostridium tyrobutyricum* | WS 2762 | | no |
| *Clostridium tyrobutyricum* | WS 2763 | | no |
| *Clostridium tyrobutyricum* | WS 2764 | | no |
| *Clostridium tyrobutyricum* | WS 2765 | | no |
| *Clostridium tyrobutyricum* | WS 2766 | | no |
| *Clostridium tyrobutyricum* | WS 2767 | | no |
| *Clostridium tyrobutyricum* | WS 2768 | | no |
| *Clostridium tyrobutyricum* | WS 2769 | | no |
| *Escherichia coli* | WS 1329 | | no |
| *Lactobacillus ruminis* | WS 2560 | | no |
| *Lactococcus lactis* | WS 1030 | | no |
| *Salmonella enterica* Group IV | WS 2870 | | no |
| *Enterobacter cloacae* | WS 1294 | | no |

Figure 5:
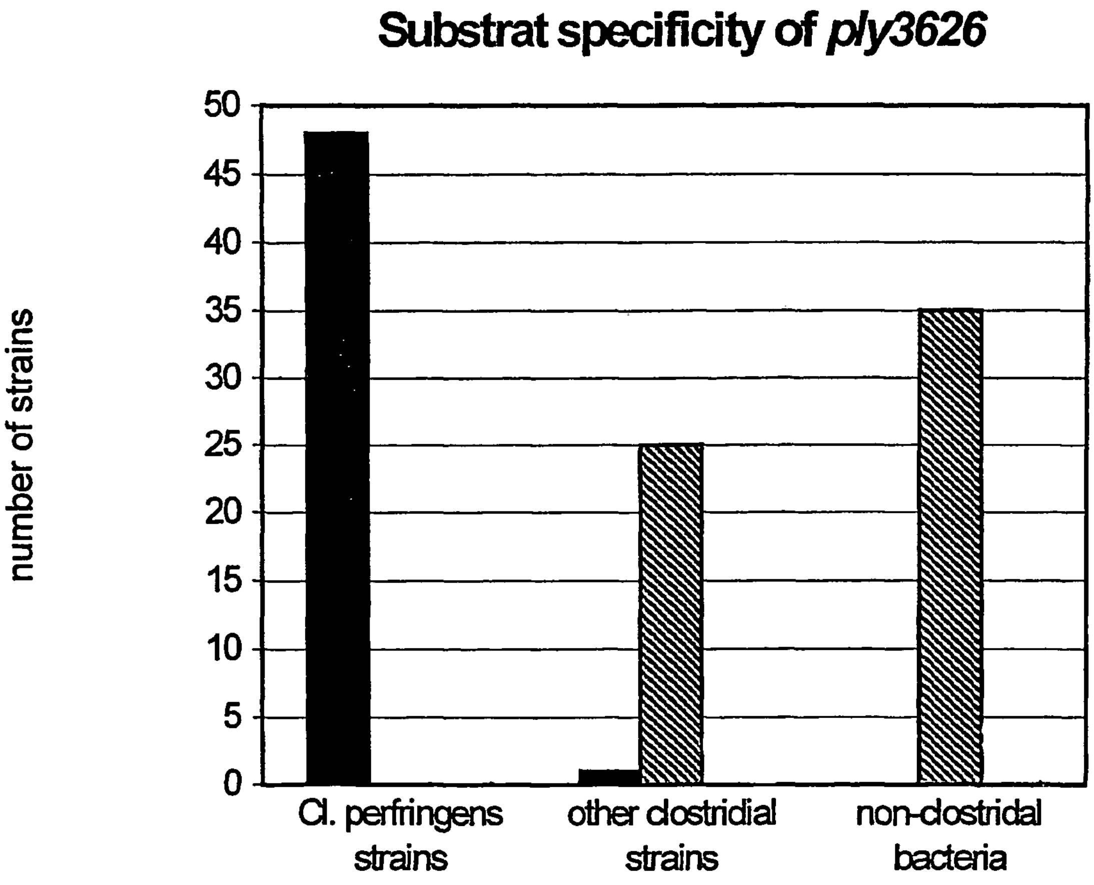
FIG. 5 shows a graph of substrate specificity of a lysin from *C. perfringens* bacteriophage ϕ3626 against various bacterial species and genera.

Results: As shown in FIG. 5 all 48 *C. perfringens* strains were sensitive to the lysin according the present invention.

Only one further clostridial species showed any sensitivity which was *C. fallax* strain DSM 2631. The sensitivity of *Cl. fallax* might be due to cell wall structure of this clostridial species, which is the same as for *C. perfringens* in having the peptidoglycan of the A3γ group in being cross-linked via LL-DAP with a glycine building the interbridge (see Schleifer et al 1972 Bacteriol Rev. 36: 407-77).

Of all the other bacteria tested (whether other clostridial species, such as *C. botulinum, C. tetani, C. novyi, C. tyrobutyricum*, or non-clostridial bacteria, such as *Bacillus, Campylobacter, Leuconostoc, Lactobacillus, Lactococcus, Pediococcus, Enterobacter, E. coli, Listeria, Bifidobacterium, Enterococcus, Streptococcus, Staphylococcus*)—60 in total—none were found to be non-sensitive to the lysin according to the present invention.

CONCLUSION

Thus, surprisingly a lysin isolated and sequenced from a bacteriophage of *Clostridium perfringens* is species specific or is substantially species specific to *C. perfringens*. The advantage of such species specificity is that the administration of said lysin to a subject will result is selective destruction of *Clostridium perfringens* and/or *C. fallax* (both pathogenic *Clostridium* species) without harming beneficial and/or harmless bacteria.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An isolated lysin comprising the amino acid sequence of SEQ ID NO:2.

2. A pharmaceutical composition comprising an isolated lysin comprising the amino acid sequence of SEQ ID NO:2.

3. The pharmaceutical composition according to claim 2, wherein the composition comprises a pharmaceutically acceptable diluent, excipient or carner.

4. A medicament comprising the lysin of claim 1.

5. A method of treating a disorder, disease or condition caused by a *Clostridium perfringens* or *Clostridium fallax* bacterium in a subject comprising administering to said subject an effective amount of an isolated lysin comprising the amino acid sequence of SEQ ID NO:2, wherein said isolated lysin lyses said bacterium.

6. A pharmaceutical pack comprising one or more compartments, wherein at least one compartment comprises an isolated lysin comprising the amino acid sequence of SEQ ID NO:2.

7. A process of preparation of a pharmaceutical composition comprising admixing an isolated lysin comprising the amino acid sequence of SEQ ID NO:2 with a pharmaceutically acceptable diluent, excipient or carrier.

8. A method of lysing a pathogenic bacterium selected from *Clostridium perfringens* or *Clostridium fallax* comprising contacting said bacterium with an isolated lysin comprising the amino acid sequence of SEQ ID NO:2.

9. The method according to claim 8, wherein said *Clostridium* bacterium is in the intestinal tract of a subject.

10. A method of detecting a *Clostridium* bacterium in a sample comprising contacting said sample with either:

(a) a diagnostic marker comprising
  (i) an isolated lysin comprising the amino acid sequence of SEQ ID NO:2, and
  (ii) a detectable marker; or
(b) an isolated lysin comprising the amino acid sequence of SEQ ID NO:2, and either detecting said diagnostic marker bound to said bacterium in said sample, or detecting the lysis of said bacterium by said isolated lysin.

11. The method according to claim 10, wherein said *Closiridium* bacterium is of the species *Clostridium perfringens* or *Clostridium fallax*.

12. The method according to claim 10, wherein said detecting comprises detecting said detectable marker bound to said bacterium.

13. The method of claim 5, wherein said disorder, disease or condition is selected from the group consisting of necrotic enteritis, gas gangrene, food poisoning, gut lesions or reduced weight.

14. The method according to claim 10, wherein detecting comprises detecting a lysis product from said bacterium.

* * * * *

UNITED STATES PATENT AND TRADEMARK OFFICE

CERTIFICATE OF CORRECTION

PATENT NO. : 7,371,375 B2
APPLICATION NO. : 10/503556
DATED : May 13, 2008
INVENTOR(S) : Markus Zimmer et al.

It is certified that error appears in the above-identified patent and that said Letters Patent is hereby corrected as shown below:

In title page, item (54) Title, delete “PROTEIN” and insert --BACTERIOPHAGE LYSIN-- therefor.

In title page, item (75) Inventors, lines 3-4, delete “Haywards Heath” and insert --West Sussex-- therefor.

In title page, item (73) Assignee, delete “Regensgurg” and insert --Regensburg-- therefor.

In column 1, line 1, delete “PROTEIN” and insert --BACTERIOPHAGE LYSIN-- therefor.

In claim 3, column 45, line 31, delete “carner” and insert --carrier-- therefor.

In claim 11, column 46, line 38, delete “*Closiridium*” and insert --*Clostridium*-- therefor.

Signed and Sealed this

Fifth Day of August, 2008

JON W. DUDAS
*Director of the United States Patent and Trademark Office*

```
                    SEQUENCE LISTING

<160> NUMBER OF SEQ ID NOS: 2

<210> SEQ ID NO 1
<211> LENGTH: 1044
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1

atgaagatag cagaaagagg cggtcataat tttcaagcta caggagcagt aggattaata     60

aatgaaacag tagaggatag aaaagtatta gcagctgcat acaaatatac taaagcggca    120

ggatacgatg tattagatgt aacaccaggc aattgtgatt ctaatacaga tttaatttta    180

ggagttaaca aggctgaaag atttggagct gaattattct taagttatca ttttgataaa    240

tgctatgatg aatacaatgg agctttagga gttgcttgtt ggatttgtgc tactggtggg    300

aaagcagaag aatacgctaa aagcatagtt gatactatag cagcaggaac aggattaaaa    360
```

```
aatagagggg ttaaagtaaa tcctaagctt tatgaattaa ggaaaacatc tatgccagca    420

gttatagttg aggtatgctt ctgtgaagcg actgaggatg ttagaattta caaagaaaaa    480

ggtgcagatt taataggtaa attaatagca gaaggagttt gtaaagttgc tgggggacaa    540

gttccaggaa cagtaataga aaatgtagaa tatgaagtgc aagaatctaa accagttcca    600

gtttatgata gaaataaatt taaaactaat gcaagagctt tagttaattt agatccaaga    660

gatagagcaa gtggaatata tgaagattta ggcgaaattt ataaggatga aagattttat    720

gtacttccag aggtttgtga taaaggtgat tatctgccag ttctttattg gaaagatgga    780

gcaaatagag catctaataa agtatgggta agtagtaaac aaaaatatat gatgatagac    840

acttatcata gagtagttaa tgttgttaca gagttagatg ctagatatga gccttctcct    900

aactcaaata gaatgggcta cgtatgcaat gctgaaagag tatatgttca taagatagaa    960

ggaaactatg cattatgtac atattttgca ggagaaggct ataaaacagc atggtttaca   1020

gctaaatatt tagaaagaat ataa                                          1044


<210> SEQ ID NO 2
<211> LENGTH: 347
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Met Lys Ile Ala Glu Arg Gly Gly His Asn Phe Gln Ala Thr Gly Ala
  1               5                  10                  15

Val Gly Leu Ile Asn Glu Thr Val Glu Asp Arg Lys Val Leu Ala Ala
             20                  25                  30

Ala Tyr Lys Tyr Thr Lys Ala Ala Gly Tyr Asp Val Leu Asp Val Thr
         35                  40                  45

Pro Gly Asn Cys Asp Ser Asn Thr Asp Leu Ile Leu Gly Val Asn Lys
     50                  55                  60

Ala Glu Arg Glu Gly Ala Glu Leu Phe Leu Ser Tyr His Phe Asp Lys
 65                  70                  75                  80

Cys Tyr Asp Glu Tyr Asn Gly Ala Leu Gly Val Ala Cys Trp Ile Cys
                 85                  90                  95

Ala Thr Gly Gly Lys Ala Glu Glu Tyr Ala Lys Ser Ile Val Asp Thr
            100                 105                 110

Ile Ala Ala Gly Thr Gly Leu Lys Asn Arg Gly Val Lys Val Asn Pro
        115                 120                 125

Lys Leu Tyr Glu Leu Arg Lys Thr Ser Met Pro Ala Val Ile Val Glu
    130                 135                 140

Val Cys Phe Cys Glu Ala Thr Glu Asp Val Arg Ile Tyr Lys Glu Lys
145                 150                 155                 160

Gly Ala Asp Leu Ile Gly Lys Leu Ile Ala Glu Gly Val Cys Lys Val
                165                 170                 175

Ala Gly Gly Gln Val Pro Gly Thr Val Ile Glu Asn Val Glu Tyr Glu
            180                 185                 190

Val Gln Glu Ser Lys Pro Val Pro Val Tyr Asp Arg Asn Lys Phe Lys
        195                 200                 205

Thr Asn Ala Arg Ala Leu Val Asn Leu Asp Pro Arg Asp Arg Ala Ser
    210                 215                 220

Gly Ile Tyr Glu Asp Leu Gly Glu Ile Tyr Lys Asp Glu Arg Phe Tyr
```

-continued

```
225                 230                 235                 240

Val Leu Pro Glu Val Cys Asp Lys Gly Asp Tyr Leu Pro Val Leu Tyr
                245                 250                 255

Trp Lys Asp Gly Ala Asn Arg Ala Ser Asn Lys Val Trp Tyr Ser Ser
            260                 265                 270

Lys Gln Lys Tyr Met Met Ile Asp Thr Tyr His Arg Val Val Asn Val
        275                 280                 285

Val Thr Glu Leu Asp Ala Arg Tyr Glu Pro Ser Pro Asn Ser Asn Arg
    290                 295                 300

Met Gly Tyr Val Cys Asn Ala Glu Arg Val Tyr Val His Lys Ile Glu
305                 310                 315                 320

Gly Asn Tyr Ala Leu Cys Thr Tyr Phe Ala Gly Glu Gly Tyr Lys Thr
                325                 330                 335

Ala Trp Phe Thr Ala Lys Tyr Leu Glu Arg Ile
            340                 345
```